US010376522B2

(12) United States Patent
Arbiser

(10) Patent No.: US 10,376,522 B2
(45) Date of Patent: *Aug. 13, 2019

(54) TRIARYLMETHANE ANALOGS AND THEIR USE IN TREATING CANCERS

(71) Applicants:Emory University, Atlatna, GA (US); U.S. Government as Represented by The Department of Veterans Affairs, Washington, DC (US)

(72) Inventor: Jack L. Arbiser, Atlanta, GA (US)

(73) Assignees: Emory University, Atlanta, GA (US); U.S. Government as Represented by the Dept. of VA, Washington, DC (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/173,946

(22) Filed: Jun. 6, 2016

(65) Prior Publication Data

US 2017/0000801 A1    Jan. 5, 2017

Related U.S. Application Data

(63) Continuation of application No. 13/412,895, filed on Mar. 6, 2012, now Pat. No. 9,358,226, which is a continuation of application No. 12/345,652, filed on Dec. 29, 2008, now abandoned.

(60) Provisional application No. 61/090,027, filed on Aug. 19, 2008, provisional application No. 61/009,745, filed on Dec. 31, 2007.

(51) Int. Cl.
| | |
|---|---|
| *A61K 31/55* | (2006.01) |
| *A61K 9/127* | (2006.01) |
| *C07D 223/28* | (2006.01) |
| *A61K 31/136* | (2006.01) |
| *A61K 31/14* | (2006.01) |
| *A61K 31/353* | (2006.01) |
| *A61K 31/404* | (2006.01) |
| *A61K 31/422* | (2006.01) |
| *A61K 31/428* | (2006.01) |
| *A61K 31/47* | (2006.01) |
| *A61K 31/4706* | (2006.01) |
| *A61K 31/4709* | (2006.01) |
| *A61K 31/54* | (2006.01) |
| *A61K 31/553* | (2006.01) |
| *A61K 31/662* | (2006.01) |
| *C07D 223/26* | (2006.01) |
| *C07F 9/40* | (2006.01) |
| *C07D 215/26* | (2006.01) |
| *C07D 215/46* | (2006.01) |
| *C07D 263/32* | (2006.01) |
| *C07D 275/06* | (2006.01) |
| *C07D 279/28* | (2006.01) |
| *C07D 311/36* | (2006.01) |

(52) U.S. Cl.
CPC .............. *A61K 31/55* (2013.01); *A61K 9/127* (2013.01); *A61K 31/136* (2013.01); *A61K 31/14* (2013.01); *A61K 31/353* (2013.01); *A61K 31/404* (2013.01); *A61K 31/422* (2013.01); *A61K 31/428* (2013.01); *A61K 31/47* (2013.01); *A61K 31/4706* (2013.01); *A61K 31/4709* (2013.01); *A61K 31/54* (2013.01); *A61K 31/553* (2013.01); *A61K 31/662* (2013.01); *C07D 215/26* (2013.01); *C07D 215/46* (2013.01); *C07D 223/26* (2013.01); *C07D 223/28* (2013.01); *C07D 263/32* (2013.01); *C07D 275/06* (2013.01); *C07D 279/28* (2013.01); *C07D 311/36* (2013.01); *C07F 9/4056* (2013.01); *C07F 9/4059* (2013.01)

(58) Field of Classification Search
CPC ............................... A61K 31/55; A61K 9/127
See application file for complete search history.

(56) References Cited

U.S. PATENT DOCUMENTS

| | | |
|---|---|---|
| 3,760,007 A | 9/1973 | Steinman |
| 8,435,979 B2 | 5/2013 | Arbiser |
| 9,358,226 B2 | 6/2016 | Arbiser |
| 2002/0123531 A1 | 9/2002 | Indig et al. |
| 2009/0176745 A1 | 7/2009 | Arbiser |
| 2010/0160296 A1 | 6/2010 | Fischer |

FOREIGN PATENT DOCUMENTS

| | | |
|---|---|---|
| WO | 2009/088838 | 7/2009 |
| WO | 2010/124004 | 10/2010 |

OTHER PUBLICATIONS

Vippagunta et al. Advanced Drug Delivery Reviews, 2001, vol. 48, pp. 3-26.
Indig, G. et al., "Effect of dye aggregation on triarylmethane-mediated photoinduced damage of hexokinase and DNA", "Journal of Photochemistry and Photobiology", 2002, pp. 139-148, vol. 67.
Munson et al. Anti-Invasive Adjuvant Therapy with Imipramine Blue Enhances Chemotherapeutic Efficacy Against Glioma Sci Transl Med 4, 127ra36 (2012).
Funding et al. Mitogen- and Stress-Activated Protein Kinase IIs Activated in Lesional Psoriatic Epidermis and Regulates the Expression of Pro-InflammatoryCytokines Journal of Investigative Dermatology (2006) 126, 1784-1791.

*Primary Examiner* — Samira J Jean-Louis
(74) *Attorney, Agent, or Firm* — Meunier Carlin & Curfman LLC

(57) ABSTRACT

Compounds, pharmaceutical compositions including the compounds, and methods of preparation and use thereof are disclosed. The compounds are triphenyl methane analogs. The compounds and compositions can be used to treat and/or prevent a wide variety of cancers, including drug resistant cancers, inflammatory, degenerative and vascular diseases, including various ocular diseases, and parasitic infections. Representative triphenyl methane analogs include triphenyl methane analogs of various dyes, hormones, sugars, peptides, oligonucleotides, amino acids, nucleotides, nucleosides, and polyols. The compounds are believed to function by inhibiting tNOX expression, the effects of ROS, and/or the production of HIF2. Thus, the compounds are novel therapeutic agents for a variety of cancers and other diseases.

4 Claims, 18 Drawing Sheets

Tumor volume (mm$^3$) of bEnd. 3 mice treated with brilliant green or gentian violet

Activity of TPM 10 at Treating Leishmania Infection
(Measured at 48 hours exposure)

TRIARYLMETHANE ANALOGS AND THEIR USE IN TREATING CANCERS

CROSS-REFERENCE TO RELATED APPLICATIONS

This application claims the benefit of U.S. Provisional Patent Application No. 61/009,745 filed Dec. 31, 2007, and U.S. Patent Application No. 61/090,027 filed Aug. 19, 2008. The disclosures of all of the foregoing applications are hereby incorporated herein in their respective entireties, for all purposes.

GOVERNMENT RIGHTS IN INVENTION

Some aspects of the invention disclosed in this application were supported by the United States government, National Institute of Health Grant No. AR02030. Accordingly, the U.S. Government has certain rights in the invention hereof.

This invention was made with government support under grant number AR02030 awarded by the National Institutes of Health. The government has certain rights in the invention.

FIELD OF THE INVENTION

The present invention relates to novel methods and compositions for the treatment of primary and metastatic cancers and other proliferative disorders. These methods and compositions use triarylmethanes. These compounds, and pharmaceutical compositions including the compounds, are particularly useful for treating primary and metastatic cancers in humans. The invention also encompasses the varying modes of administration of the therapeutic compounds or compositions.

BACKGROUND OF THE INVENTION

Cancer is characterized primarily by an increase in the number of abnormal cells derived from a given normal tissue, invasion of adjacent tissues by these abnormal cells, and lymphatic or blood-borne spread of malignant cells to regional lymph nodes and to distant sites (metastasis). Cancer is a multistep process, beginning with minor preneoplastic changes, which may under certain conditions progress to neoplasia. Malignant endothelial tumors arise in the setting of autocrine loops involving vascular endothelial growth factor (VEGF) and its major mitogenic receptor vascular endothelial growth factor receptor 2.

Reactive oxygen species (ROS) are believed to be mediators of growth and angiogenesis in cancer. Increased ROS often correlates with cell growth, e.g., Ras-transformed cells and cells treated with growth factors. While non-transformed cells respond to growth factors/cytokines with the regulated production of ROS, tumor cells in culture frequently overproduce $H_2O_2$.

NAD(P)H oxidase (Nox) is a cell surface protein with hydroquinone (NADH) oxidase and protein disulfide-thiol interchange activities. In general, most forms of the enzyme can utilize either NADH or NADPH equally efficiently. There are many forms of Nox, including Nox 1-5, Dual oxidase 1 and 2 (Duox 1 and 2), as well as p22(phox), p47(phox) and the small G-protein Rac1.

Nox are believed to account for increased levels of ROS in certain cancers. Reactive oxygen-generating Nox enzymes are implicated in the angiogenic switch, and Nox inhibitors have an effect on ang-2 production in vitro and on bEnd.3 tumor growth in vivo. ang-2 production can be inhibited pharmacologically using Nox enzyme inhibitors, which nearly abolishes bEnd.3 hemangioma growth in vivo. Signal-transduction blockade targeting ang-2 production may therefore be useful for treating human hemangiomas in vivo. Journal of Investigative Dermatology advance online publication, 1 Jun. 2006; doi:10.1038/sj.jid.5700413.

With respect to specific Nox enzymes, it has been shown that transfection of Nox1 into a prostate cancer cell line dramatically enhanced tumor growth (Arbiser et al.: PNAS 99:715-720, 2001), and prostate tumors show increased $H_2O_2$ levels. Further, prostate tumors were recently found to show increased levels of Nox1 and hydrogen peroxide (Lim et al., Prostate, 2005 Feb. 1; 62(2):200-7). Nox1-dependent superoxide production has also been shown to control colon adenocarcinoma cell migration (Sadok et al., *Biochim. Biophys. Acta.* 1783(1):23-33 (January 2008). Sadok showed that Nox1 inhibition or down-regulation led to a decrease of superoxide production and alpha 2 beta 1 integrin membrane availability. Thus, there is a correlation between Nox protein levels and ROS in prostate cancer, and increased Nox1/$H_2O_2$ correlates with increased tumorigenicity.

Nox4 is believed to be implicated in inhibition of apoptosis in cancer cells, such as pancreatic cancer cells (Vaquero et al., *J Biol Chem.* 2004 Aug. 13; 279(33):34643-54). Vaquero suggested that growth factor-induced ROS produced by NAD(P)H oxidase (probably Nox4) protects pancreatic cancer cells from apoptosis, and that transfection with a Nox4 antisense oligonucleotide inhibited NAD(P)H oxidase activity and ROS production in certain pancreatic cells (i.e., MIA PaCa-2 and PANC-1 cells), and stimulated apoptosis in these cells.

Akt, a signaling molecule downstream of PI3K (phosphoinositol-3-kinase), is known to induce expression of the ROS-generating enzyme Nox4. One study introduced Akt into a radial growth WM35 melanoma in order to test whether Akt overexpression was sufficient to transform the cells from radial growth to vertical growth. Overexpression of Akt led to upregulation of VEGF, increased production of superoxide ROS, and the switch to a more pronounced glycolytic metabolism. Subcutaneous implantation of WM35 cells overexpressing Akt led to rapidly growing tumors in vivo, while vector control cells did not form tumors. Arbiser et al., *J. Invest. Dermatol.* 2006. Jun. 1, 16741507. This data supports the premise that inhibition of Akt can inhibit downstream production of Nox 4, which then would inhibit superoxide generation, and therefore treat melanoma.

Duox 1 and 2 are the major Nox species in airway endothelia, and are believed to be one of the main sources for reactive oxygen species production in the airway (Luxen et al., *Cancer Res.* 2008 Feb. 15; 68(4):1037-45). Accordingly, inhibition of these enzymes may be useful in treating human lung cancer.

Some authors have characterized Nox as falling into two categories. One is hormone-insensitive and drug-responsive (i.e., by quinine-site inhibitors such as capsaicin or the antitumor sulfonylurea, LY181984), designated "tNox," which is specific to cancer cells. The other is a drug-indifferent constitutive form associated with the plasma membrane of non-transformed cells, designated "CNox" (Kelker et al., Biochemistry. 26; 40(25):7351-4 (2001); Wang et al., Biochim Biophys Acta. June 20; 1539(3): 192-204 (2001)

Cancer cells exhibit both drug-responsive and hormone and growth factor-indifferent (tNox), and drug inhibited and hormone and growth factor dependent (CNox) activities, whereas non-transformed cells exhibit only the drug indifferent hormone- and drug-responsive CNox. Like the tNox of cancer cells, CNox is capable of oxidizing NADH, but has an activity which is modulated by hormones and growth factors. Thus, some authors have theorized that inhibitors of tNox (which are believed to include one or more of the Nox enzymes listed above, such as Nox4) will be useful for treating cancer.

In addition to treating cancer, Nox inhibitors are also expected to provide therapeutic effects for numerous other inflammatory, degenerative and vascular diseases in which reactive oxygen species have been implicated.

For example, Nox has been reported to have a role in retinal vascular inflammation, as well as ischemia-induced increases in vascular endothelial growth factor (VEGF) and retinal neovascularization (Al-Shabrawey et al., *Invest. Ophthalmol. Vis, Sci.* (2008). Studies performed using wild type mice, mice lacking Nox2 and mice treated with the NADPH oxidase inhibitor apocynin in models of endotoxemia and streptozotocin-induced diabetes showed that both endotoxemia- and diabetes-induced increases in ICAM-1 expression and leukostasis were significantly inhibited by deletion of Nox2. Apocynin treatment was as effective as deletion of Nox2 in preventing diabetes-induced increases in ICAM-1, leukostasis, and breakdown of the blood-retinal barrier, suggesting that Nox2 is primarily responsible for these early signs of diabetic retinopathy.

Elevated ROS initiate and anti-oxidants inhibit the apoptotic cell loss in the retinal pigment epithelium (Glotkin et al, 2006 IOVS, 47: 4614-4623). This is thought to play a role in the development of dry age-related macular degeneration. Likewise, the use of antioxidants had been shown to reduce the progression to neovascularization in patients with large drusen in AMD (Coleman and Chew, 2007, Curr. Opin. Ophthalmol. 18(3): 220-223).

NADP+ reductases lower the concentration of retinaldehyde and retinoic acid, which in turn protect cells from retinaldehyde-induced cell death (Lee et al., J. Biol. Chem., 282(49)35621-8 (2007). By extension, inhibition of NADPH oxidase can have the same effect as increasing the rate of a NADP+ reductase, and have a beneficial effect on retinal degeneration mediated by retinaldehyde or retinoic acid.

Specific inhibition of NADPH oxidase has been shown to reduce angiogenesis in models of retinopathy of prematurity (Al-Shabraway et al, 2005, Am. J. Pathol. 167(2): 599-607 and Saito et al, 2007, Mol. Vision, 13: 840-853). In addition elevated ROS have been observed in diabetic animals and the elevation correlates with increase VEGF activity. Similarly, in oxidative stress is thought to be a significant factor in the development of diabetic retinopathy (Kowluru and Chan, 2007, Expt. Diabetes Res. Article ID 43603).

ROS may have two separate effects in the development of glaucoma. First, increased ROS least to increased cellularity of the trabecular meshwork (and thereby increased intraocular pressure, Sacca et al, 2007, Exp. Eye Res. 84(3): 389-399). Over time increased reactive oxygen species may increase are also thought to stimulate apoptosis of retinal ganglion cells (Tezel, 2006, Prog. Retin. Eye Res. 25(5): 490-513), the anatomic basis of visual field loss.

In non-ocular cutaneous tissues. NADPH oxidase from pollen has been shown to perpetuate the allergic response. Inhibition of NADPH oxidase reduces mast cell degranulation and may be useful in allergic eye disease (Nishikawa et al, 2007, BBRC, 362(2): 504-509).

Although direct experimental evidence that inhibition of NADPH oxidase will provide a therapeutic effect in the some of the eye diseases mentioned is lacking, NADPH oxidase inhibition can be expected to alter the cellular redox balance and thus may be therapeutic in the various condition by indirect means.

NADPH oxidase inhibitors may also be effective for the treatment of dry eye based on the observation that NADPH oxidase is constitutively expressed in corneal epithelial and stromal cells (O'Brien et al, 2006, IOVS, 47: 853-863). The authors suggest that the production of superoxide anion may play a role in inflammation of the cornea.

With respect to the role of specific Nox enzymes in inflammatory disorders, Nox2-containing NADPH oxidase and Akt activation are believed to play a key role in angiotensin II-induced cardiomyocyte hypertrophy (Physiol. Genomics 26: 180-191, 2006).

Accordingly, Nox are believed to be responsible for increased levels of ROS in some cancers and inflammatory disorders, and treatment with appropriate inhibitors may be useful in treating such cancers and inflammatory disorders.

There remains a need for treatment of cancer that does not have the adverse effects generally caused by the non-selectivity of conventional chemotherapeutic agents. There further remains a need to have additional treatments for inflammatory, degenerative and vascular diseases in which a reactive oxygen species has been implicated. The present invention provides such compounds, compositions and methods.

SUMMARY OF THE INVENTION

Compounds, pharmaceutical compositions including the compounds, and methods of preparation and use thereof are disclosed. The compounds are triarylmethane compounds, such as triphenyl methane analogs, which can be formed, for example, by reacting a diaryl ketone such as Mischler's ketone with an aromatic or heteroaromatic compound, such as a phenol or an aniline, in the presence of a Lewis acid such as phosphorus oxychloride or thionyl chloride. Typically, an electrophilic addition occurs at the ortho or para position to hydroxy or amine groups in the phenol or aniline compounds, or meta to nitro or carboxy groups, and is followed by dehydration to form the triphenyl methane compounds.

Representative compounds include triphenyl methane analogues of steroids and steroid precursors, such as cholesterol, progesterone, testosterone, or estrogen; dyes such as indigo, chrysin, and imipramine; benzophenones, nucleosides such as uracil, thymidine, adenine, cytosine, and guanine, aromatic amino acids such as phenylalanine; folic acid, and various tricyclic compounds, including various tricyclic dyes and tricyclic antidepressants.

Specific representative compounds include the following:
[TPM1] FW=502.71 g/mol Ethylcarbazole
[TPM2] FW=588.87 g/mol Imipramine
[TPM3] FW=455.46 g/mol Mothball
[TPM4] FW=432.60 g/mol Vanillin
[TPM5] FW=512.69 g/mol Tryptophan
[TPM6] FW=400.60 g/mol Methyl Brilliant Green
[TPM7] FW=672.86 g/mol Popop Brilliant Green
[TPM8] FW=502.65 g/mol Caffeine Dye
[TPM9] FW=521.76 g/mol Proton Sponge Dye
[TPM10] FW=662.95 g/mol DDT Black The synthesis, characterization and an evaluation of the anti-tumor potential of these triarylmethane-containing compounds is also disclosed.

Prodrug forms of the compounds, in which the iminium group on certain triphenylmethanes are reduced, for example, with sodium cyanoborohydride, are also disclosed. One such compound is the reduced form of gentian violet (tris (dimethylaminophenyl) methane). The prodrugs can readily be reoxidized into the parent compounds, and offer various advantages over the drugs themselves. For example, the prodrug forms are less colored and more lipophilic (because the iminium salt is reduced to an amine). The compounds can be more easily taken up by cells than the parent drugs, and may be less irritating in vivo. In tumors/blood vessels with high levels of superoxide/hydrogen peroxide, the prodrugs can be readily oxidized to the triphenylmethane dye within the cell.

In some embodiments, the reduced compounds (prodrugs) have one or more free amine groups, which can be reacted with dichloroacetyl chloride to make one or more trichloroacetyl amide groups. Upon hydrolysis, the prodrugs will hydrolyze in vivo to form dichloroacetic acid salts ("DCA") and the triphenylmethane compounds, both of which are useful in treating cancer.

While not wishing to be bound by a particular theory, it is believed that the compounds function by one or more of the following mechanisms:

a) inhibiting all forms of Nox.
b) specifically inhibiting Nox 1-5,
c) specifically inhibiting Nox 2 and/or Nox 4 (the latter of which is more prevalent in cancer cells than normal cells),
d) inhibiting a Nox enzyme that is more prevelant in cancer cells than normal cells, hereinafter referred to as tNox,
e) inhibiting ROS,
f) promoting superoxide scavengers, such as scavenger enzyme systems catalase, superoxide dismutase I ($Zn^{2+}$/$Cu^{2+}$ SOD) and II (MN-SOD), and glutathione peroxidase, and inducing G2/M cell cycle arrest.

Evidence that the compounds can inhibit ROS is demonstrated herein in the working examples, which show that electron spin resonance spectra demonstrate that when the compounds are added to superoxide dismutase, they alter the spectra of the superoxide dismutase, and appear to be converted to a free radical.

As discussed above, the mechanism for killing the cancer cells may involve inhibition of tNOX, without significantly affecting CNox, thereby effectively inhibit cell proliferation, particularly in metastasized tumors, or the inhibition of any of the Nox enzymes, such as Nox4, which is prevalent in cancer cells. That is, in some embodiments, the Nox is one that is selectively expressed in cancer cells over normal cells, and in other embodiments, the Nox is one that is expressed in higher concentrations in cancer cells than in normal cells. In other embodiments, the compounds function by inhibiting the effects of reactive oxygen species ("ROS"), and/or by inhibiting the production of hypoxia inducible factor 2 (HIF2), which drives angiogenesis due to reactive oxygen.

Treatment with one or more of these compounds can selectively kill cancer cells, without killing healthy cells, thus providing a selective anti-cancer therapy. Most importantly, these compounds are potent against cancer cells that have become metastacized.

Data from WM35 PKB (Stable WM35 cells overexpressing Akt) suggests that the compounds can inhibit reactive oxygen in a NOX-independent fashion, for example, by directly scavenging reactive oxygen produced by defective mitochondria.

By inhibiting ROS and/or HIF2, various inflammatory, degenerative and vascular diseases in which a reactive oxygen species has been implicated can be treated.

In another embodiment, the compounds are also effective at treating parasitic infections, such as malaria, trypanosomiasis, and leishmaniasis, specifically including Chagas and sleeping sickness.

The pharmaceutical compositions include an effective amount of the compounds described herein, along with a pharmaceutically acceptable carrier or excipient. When employed in effective amounts, the compounds can act as a therapeutic agent to prevent and/or treat a wide variety of cancers, particularly metasticized cancers, and are believed to be both safe and effective in this role. Representative cancers that can be treated and/or prevented include melanoma, leukemia, non-small cell lung, colon, central nervous system (CNS), renal, ovarian, breast and prostate cancer. Additional pharmaceutical compositions may be useful for the treatment of inflammatory, degenerative and vascular diseases in which a reactive oxygen species has been implicated, specifically including ocular diseases.

The foregoing and other aspects of the present invention are explained in detail in the detailed description and examples set forth below.

BRIEF DESCRIPTION OF THE DRAWINGS

FIG. 1a shows mice with control Fc-treated tumor (left) and tie-2/Fc-treated hemangioma (right). FIG. 1b shows that hemangioma volume in mice treated with tie-2/Fc differs significantly from control mice (P<0.05). Three mice were used in each group, and the error bars represent the standard error of the mean.

In FIG. 3b, error bars represent the standard error of the mean.

DETAILED DESCRIPTION OF THE INVENTION

Figure 1A:
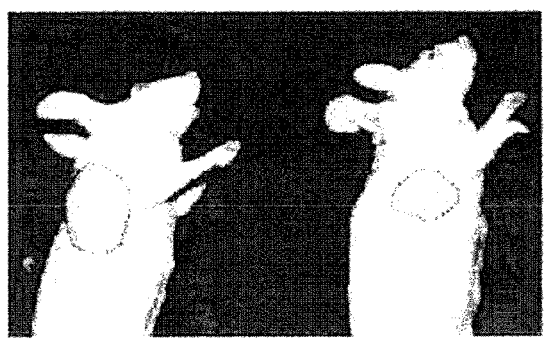
FIGS. 1a and 1b include a photograph and a chart showing that the inhibition of ang-2 signaling by a soluble tie-2 receptor inhibits bEnd.3 growth in vivo.

Compounds, pharmaceutical compositions including the compounds, and methods of preparation and use thereof are disclosed.

The following definitions will be useful in understanding the metes and bounds of the invention as described herein.

As used herein, "alkyl" refers to straight chain or branched saturated hydrocarbon radicals including $C_1$-$C_8$, preferably $C_1$-$C_5$, such as methyl, ethyl, or isopropyl; "substituted alkyl" refers to alkyl radicals further bearing one or more substituent groups such as hydroxy, alkoxy, aryloxy, mercapto, aryl, heterocyclo, halo, amino, carboxyl, carbamyl, cyano, and the like; "alkenyl" refers to straight chain or branched hydrocarbon radicals including $C_1$-$C_8$, preferably $C_1$-$C_5$ and having at least one carbon-carbon double bond; "substituted alkenyl" refers to alkenyl radicals further bearing one or more substituent groups as defined above; "cycloalkyl" refers to saturated or unsaturated, non-aromatic, cyclic ring-containing radicals containing three to eight carbon atoms, preferably three to six carbon atoms; "substituted cycloalkyl" refers to cycloalkyl radicals further bearing one or more substituent groups as defined above; the term "amino" refers to amine groups bearing zero, one, or two alkyl groups, and includes cyclic amines with ring sizes between three and eight carbons; "aryl" refers to aromatic radicals having six to ten carbon atoms; "substituted aryl" refers to aryl radicals further bearing one or more substituent groups as defined above; "alkylaryl" refers to alkyl-substituted aryl radicals; "substituted alkylaryl" refers to alkylaryl radicals further bearing one or more substituent groups as defined above; "arylalkyl" refers to aryl-substituted alkyl radicals; "substituted arylalkyl" refers to arylalkyl radicals further bearing one or more substituent groups as defined above; "heterocyclyl" refers to saturated or unsaturated cyclic radicals containing one or more heteroatoms (e.g., O, N, S) as part of the ring structure and having two to seven carbon atoms in the ring; "substituted heterocyclyl" refers to heterocyclyl radicals further bearing one or more substituent groups as defined above.

I. Compounds

The compounds are triarylmethane compounds, or prodrugs or metabolites of these compounds, and pharmaceutically acceptable salts thereof. Triarylmethane compounds typically include a first carbon-carbon double bond linked at one end to two aryl or heteroaryl rings, and at the other end to a cyclohexadiene ring (forming a "first exocyclic double bond"), which optionally includes a second exocyclic double bond, typically in the form of an imine or ketone group. The two aryl or heteroaryl rings can be linked via a bridge, which can be, for example, an alkylene bridge, such as a methylene bridge, or a heteroarom, or a direct linkage between the rings.

The second exocyclic double bond in the cyclohexadiene can be at a position "ortho" or "para" to the first exocyclic double bond.

In one embodiment, the compounds generally fall within one of the formulas provided below:

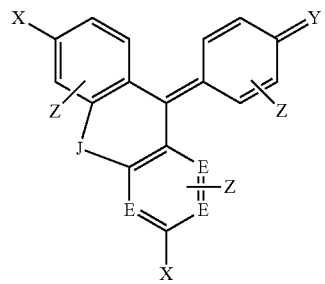

Formula 1

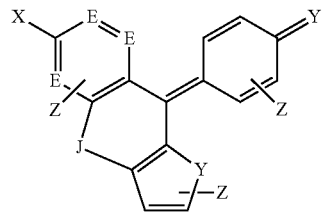

Formula 2

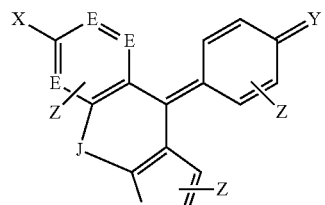

Formula 3

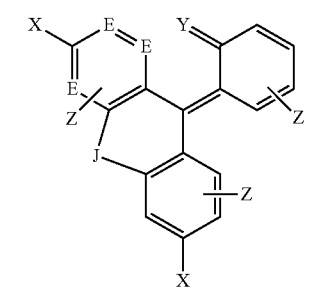

Formula 4 and counterparts to Formula 4 that include the heteroaryl rings in Formulas 2 and 3, wherein J represents a direct linkage between the two aryl rings, O, S, Se, NR, or $(CR_2)_n$, n=0-4, and, in one embodiment, is 1-4:

E is CH, C bonded to a substituent Z, as defined herein, or N,

R=H or substituted or unsubstituted alkyl, alkenyl, alkynyl, aryl, heteroaryl, alkylaryl, or arylalkyl X=H, amine, hydroxy, ether, thiol, or thiolether, and is preferably selected from amine, hydroxy, ether, thiol, and thiolether, Y=O, S, or $NR_2$, where an amine can optionally link back to the ring in an ortho position via an alkyl, alkenyl, alkynyl, alkylaryl, or arylalkyl moiety, Z=an optional substituent (e.g., halo, hydroxyl, thiol, ester, amide, carboxy, sulfoxy, nitrile, azido, alkyl, alkenyl, alkynyl, nitro, amino, aryl, heteroaryl, phosphonate, fulvene, and the like).

Z can also be a cyclic ring attached to the aryl ring, or a second aryl or heteroaryl ring attached to the benzene ring or cyclohexadiene ring.

wherein:

the aryl or heteroaryl rings can be substituted at any free position with H or a substituent, Z, as described herein.

Representative substituents, Z, include C$_{1-6}$ alkyl (including cycloalkyl), alkenyl, heterocyclyl, aryl, heteroaryl, halo (e.g., F, Cl, Br, or I), —OR', —NR'R", —CF$_3$, —CN, —NO$_2$, —C$_2$R', —SR', —N$_3$, —C(=O)NR'R", —NR'C(=O)R", —C(=O)R', —C(=O)OR', —OC(=O)R', —OC(=O)NR'R", —NR'C(=O)OR", —SO$_2$R', —SO$_2$NR'R", and —NR'SO$_2$R", where R' and R" are individually hydrogen, C$_{1-6}$ alkyl, cycloalkyl, heterocyclyl, aryl, or arylalkyl (such as benzyl);

Specific examples of compounds in which Z is a cyclic ring attached to the aryl ring, or a second aryl or heteroaryl ring attached to the benzene ring or cyclohexadiene ring, are shown below:

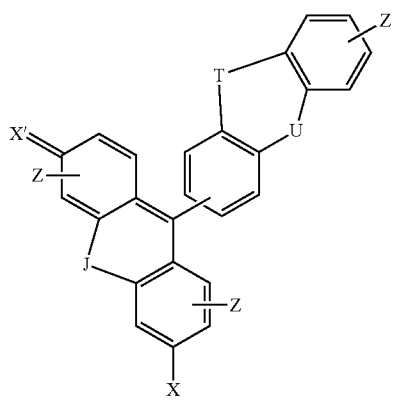

wherein
Z, X, and J are as defined above,
X' is O, S, NR, or NR$_2^+$,
T is selected from the group consisting of —C(O)—, —C(O)—O—, —C(O)—S—, —C(O)—NR—, —O—C(O)—, —S—C(O)—, —NR—C(O)—, NR, O, S, (—CR$_2$)$_n$, (—CR$_2$)$_n$—NR—, (—CR$_2$)$_n$—O—, and (—CR$_2$)$_n$—S—; and
U is selected from the group consisting of —C(O)—, NR, S, O, and (—CR$_2$)$_n$.

Representative tricyclic rings (i.e., including the U and T substituents described above) include the following:

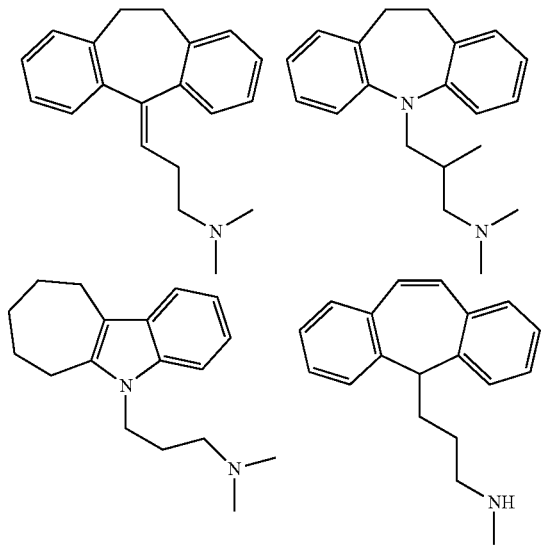

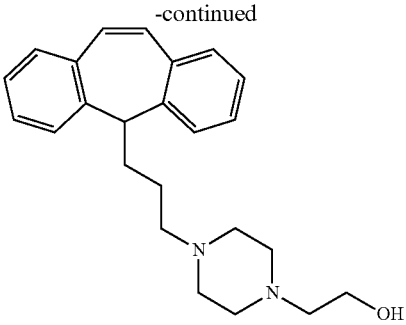

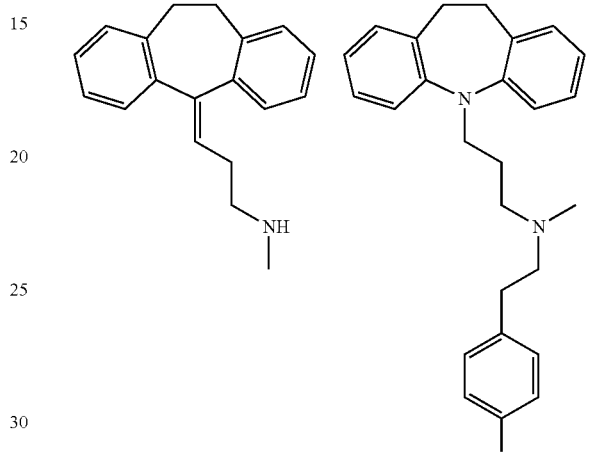

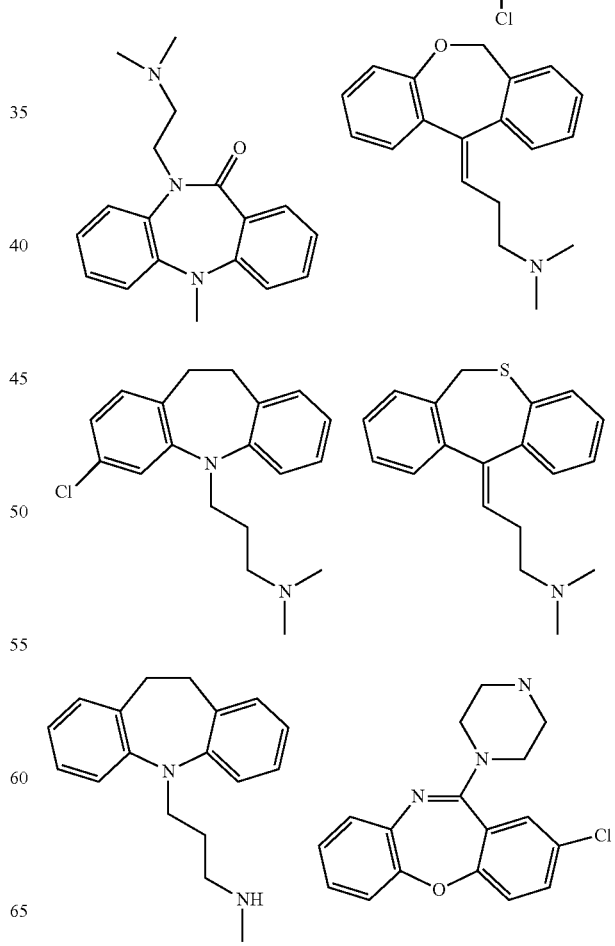

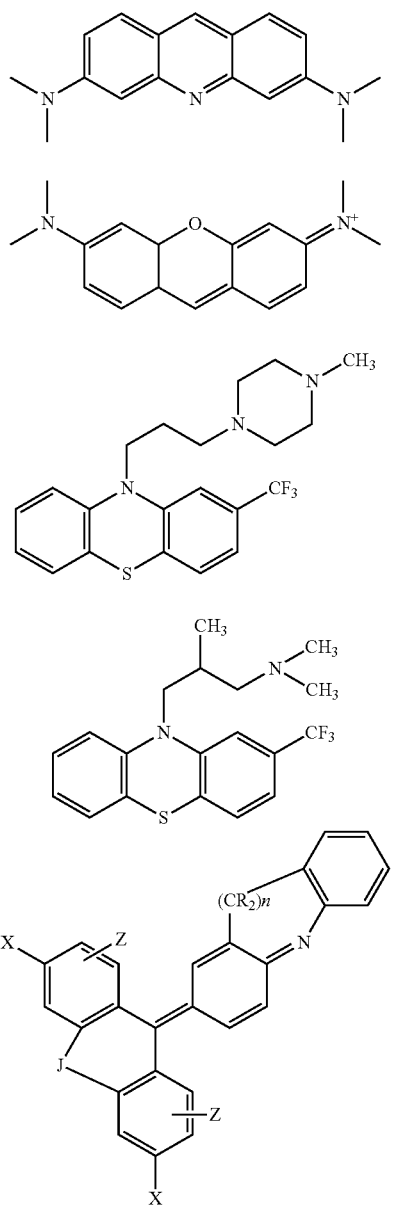

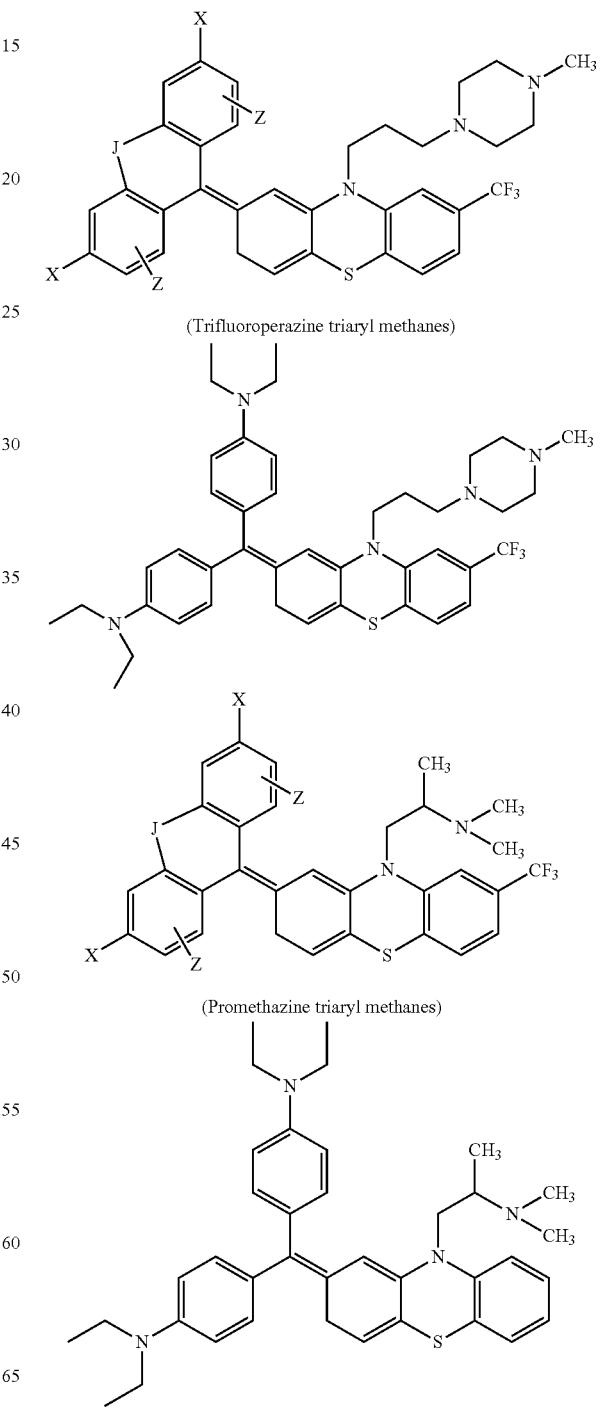

These compounds are, or are similar to, tricyclic antidepressants and triphenyl methane dyes. The aromatic rings in all of the above compounds can optionally be functionalized with one or more substituents, Z, as defined above.

The aryl rings described above are typically attached to the other aryl rings primarily at a position dictated according to the conventional rules concerning electrophilic aromatic substitution reactions. That is, those rings with an electron donating substituent, such as alkyl, aryl, alkylaryl, arylalkyl, hydroxy, ether, and amine, will tend to be substituted at a position ortho or para to that substituent, and those rings with an electron withdrawing substituent, such as nitro or carboxy, will tend to be substituted at a position meta to that substituent. Positional isomers of these compounds can be separated, or, if desired, used in combination.

In one embodiment, the compounds are similar to those in Formula 1, except that there is not an exocyclic double bond to an oxygen or nitrogen atom in the cyclohexadiene moiety. Representative compounds for this embodiment are shown below, with the definitions for the various variables being the same as those described above for Formula 1.

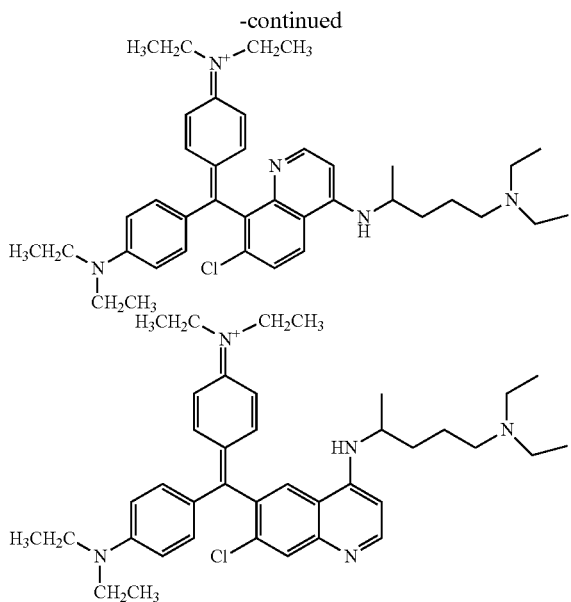

Chloroquine triaryl methanes

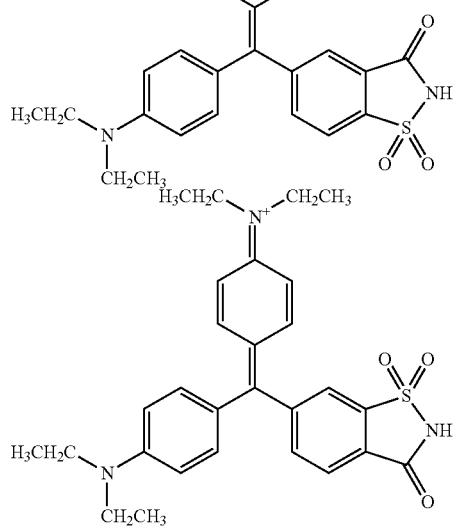

Saccharine triaryl methanes

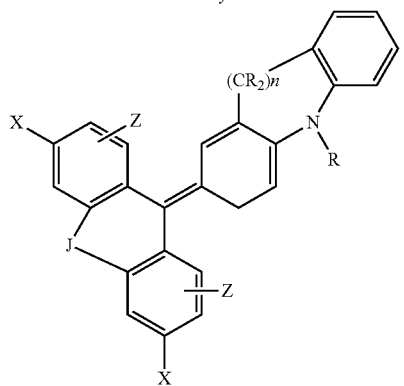

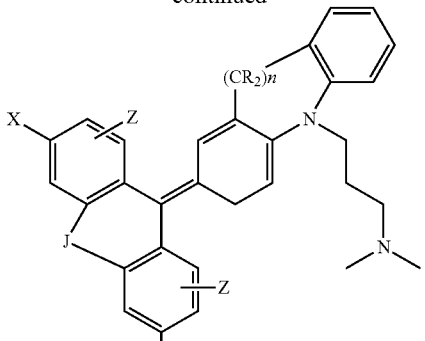

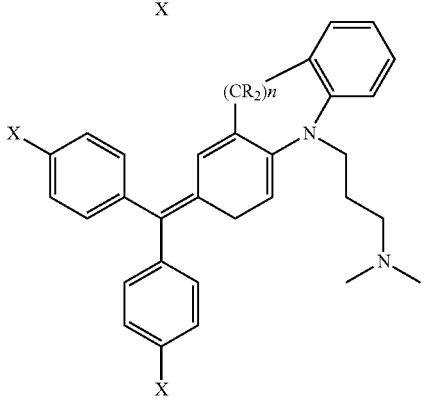

Where X, Z and R are as defined above.

The compounds can occur in varying degrees of enantiomeric excess, and racemic mixtures can be purified using known chiral separation techniques.

The compounds can be in a free base form or in a salt form (e.g., as pharmaceutically acceptable salts). Examples of suitable pharmaceutically acceptable salts include inorganic acid addition salts such as sulfate, phosphate, and nitrate; organic acid addition salts such as acetate, galactarate, propionate, succinate, lactate, glycolate, malate, tartrate, citrate, maleate, fumarate, methanesulfonate, p-toluenesulfonate, and ascorbate; salts with an acidic amino acid such as aspartate and glutamate; alkali metal salts such as sodium and potassium; alkaline earth metal salts such as magnesium and calcium; ammonium salt; organic basic salts such as trimethylamine, triethylamine, pyridine, picoline, dicyclohexylamine, and N,N'-dibenzylethylenediamine; and salts with a basic amino acid such as lysine and arginine. The salts can be in some cases hydrates or ethanol solvates. The stoichiometry of the salt will vary with the nature of the components.

The following aryl/heteroaryl rings can be present in the compounds described herein, as one of the aryl rings in Formula 1.

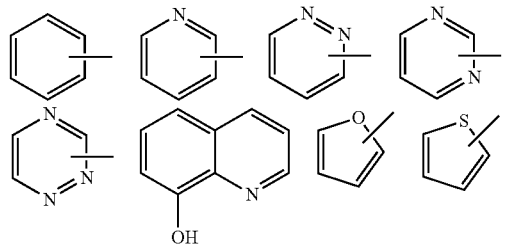

15
-continued
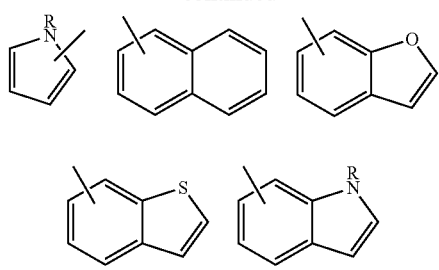
16
-continued
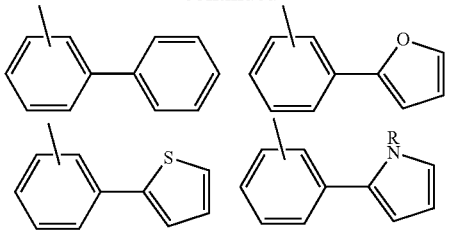
Representative compounds include the following:
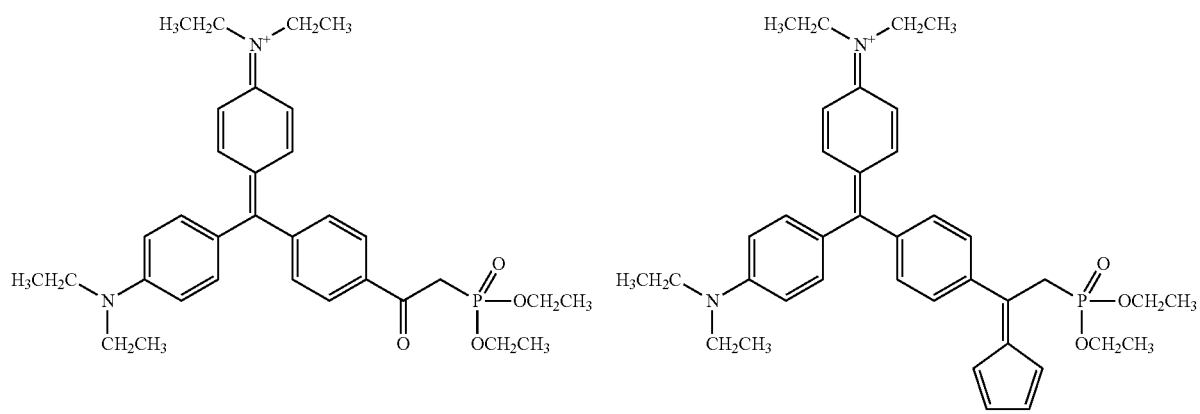
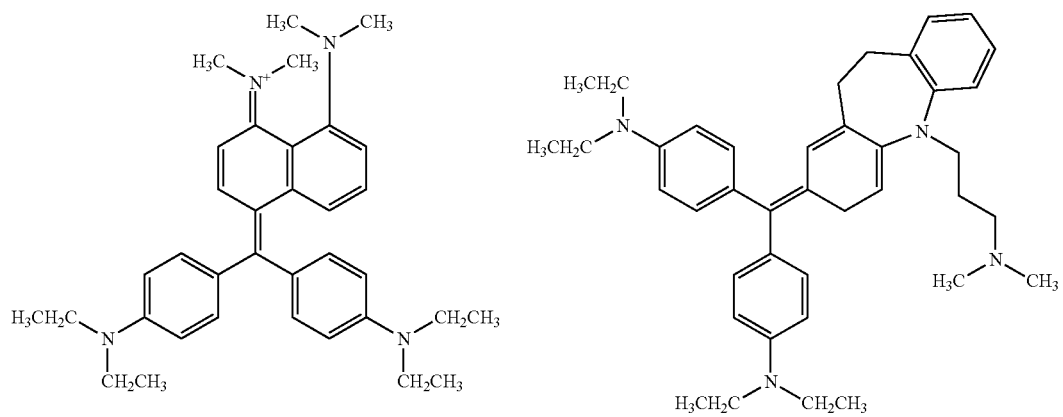
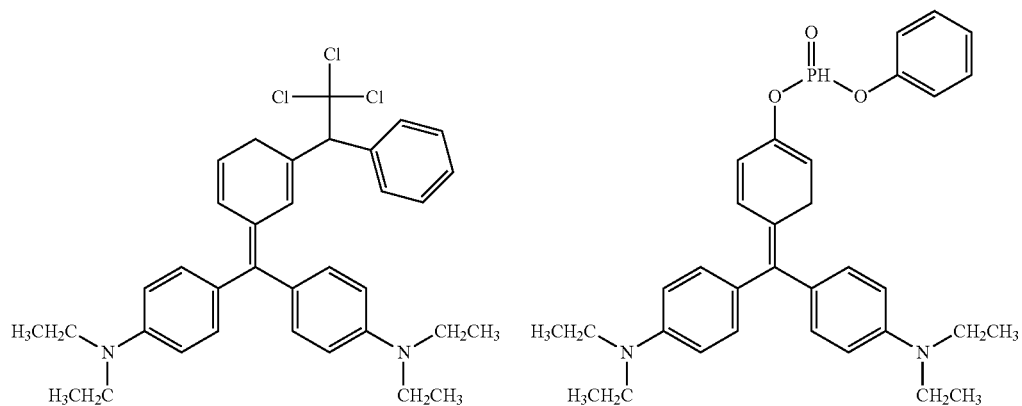

-continued
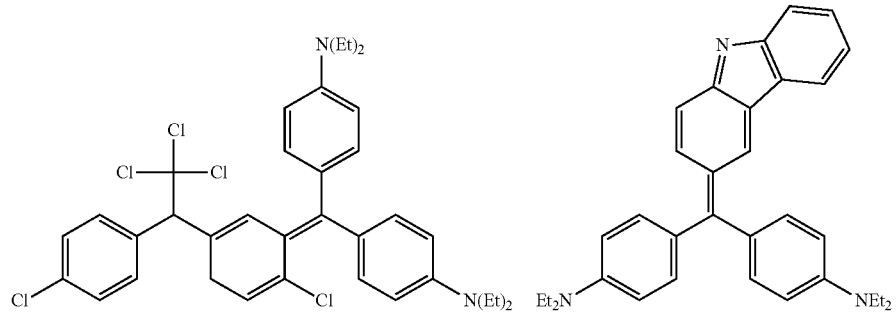
DDT Black    Carbazole Blue
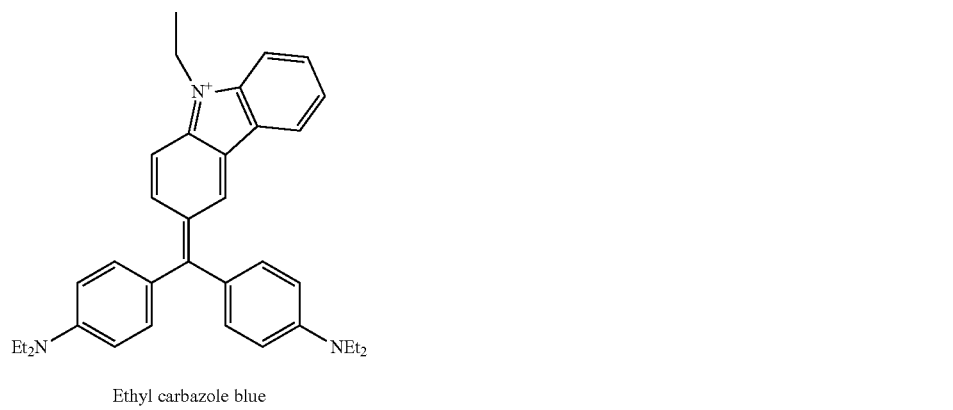
Ethyl carbazole blue
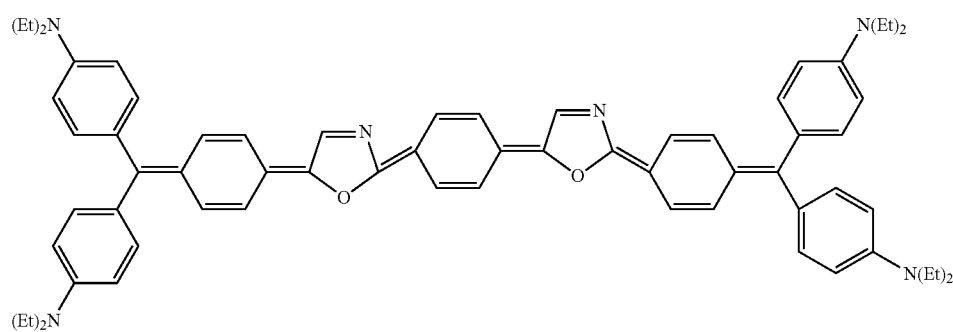
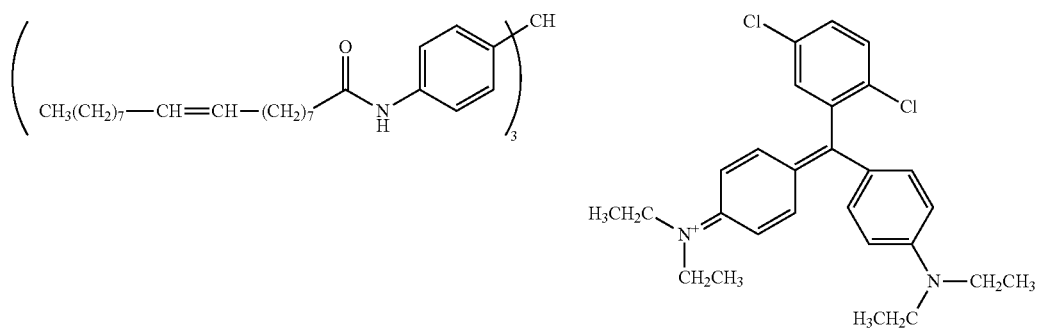

-continued
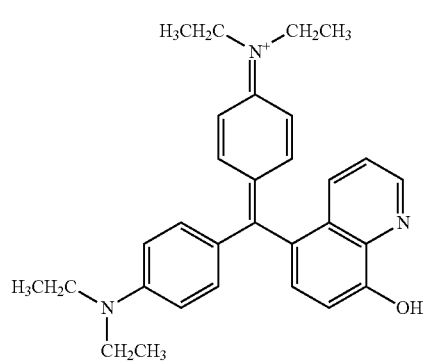
Hydroquinoline purple
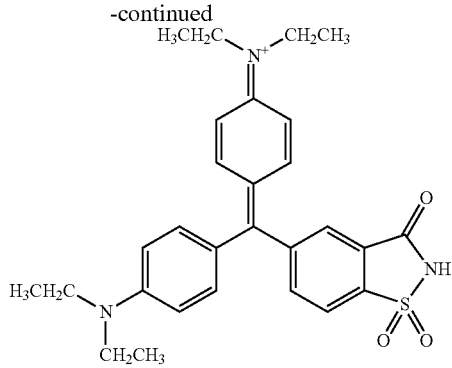
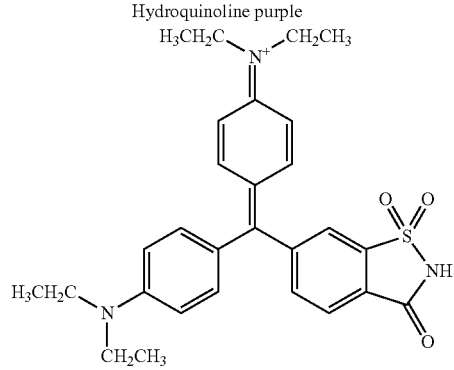
Saccharine green
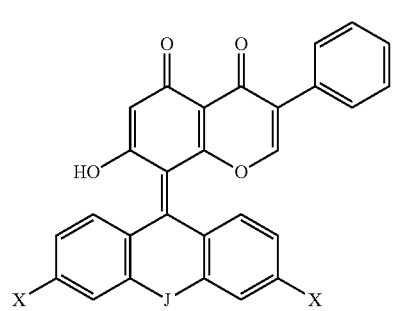
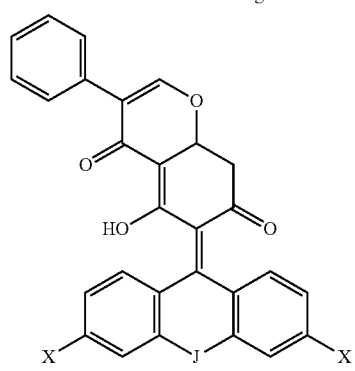
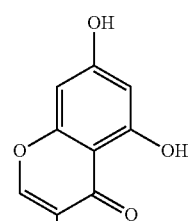
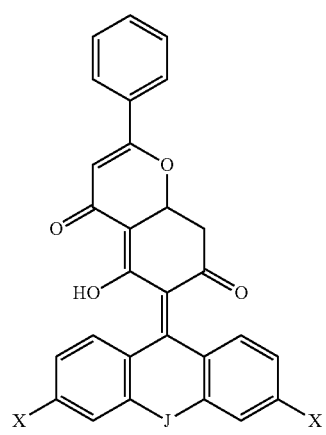
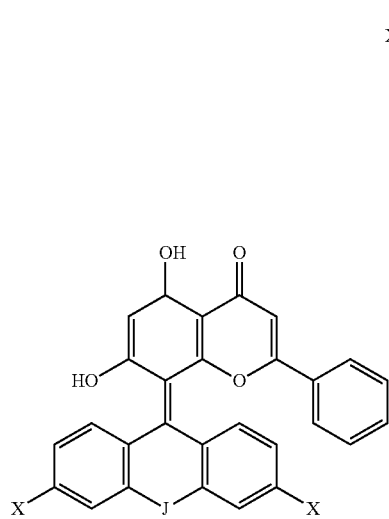
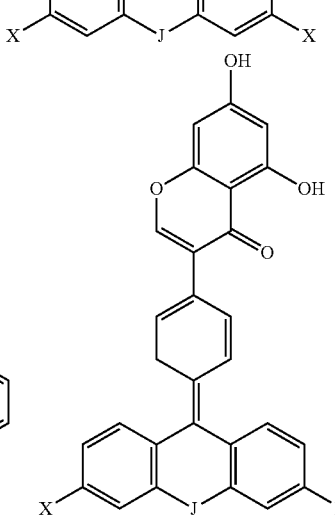
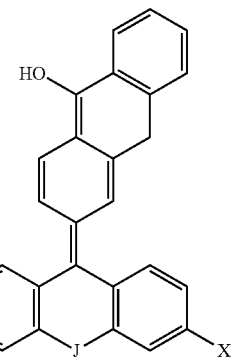

21
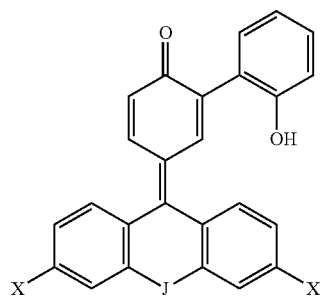
-continued
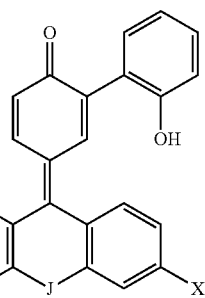
22
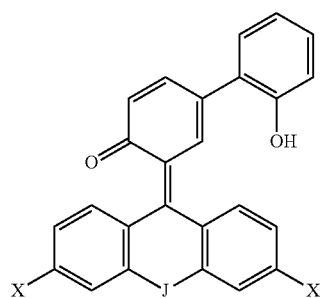
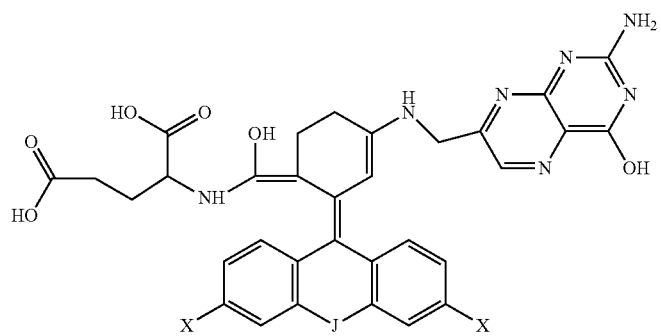
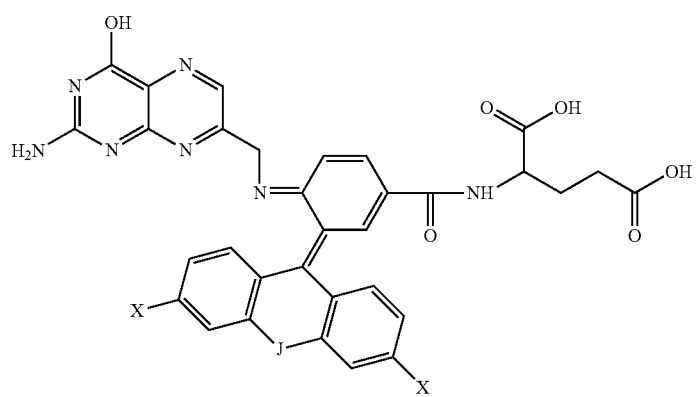
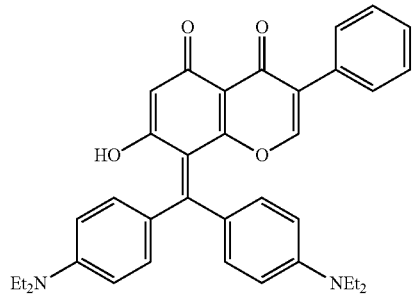
Chysin Black
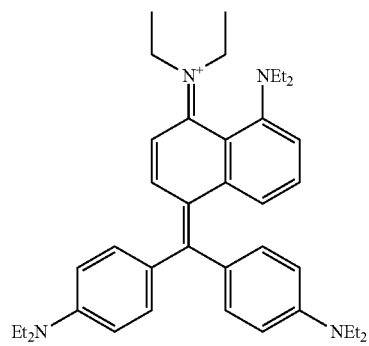
Proton Sponge
where J and X are as defined above.

Tautomeric forms of the compounds are also within the scope of the invention. For example, the compounds shown below can exist in both tautomeric forms:

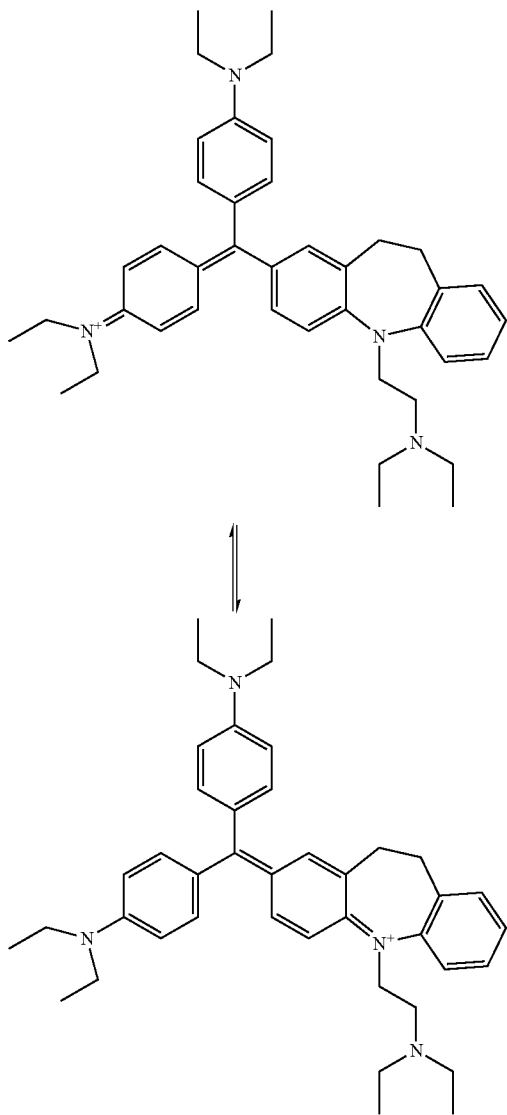 [SMILES: CCN(CC)CCN1c2ccccc2CCc2cc(C(=C3C=CC(=[N+](CC)CC)C=C3)c3ccc(N(CC)CC)cc3)ccc21 ; CCN(CC)CC[N+]1=c2ccc(=C(c3ccc(N(CC)CC)cc3)c3ccc(N(CC)CC)cc3)cc2CCc2ccccc21]

Prodrug Forms of the Compounds

In some embodiments, the reduced compounds (prodrugs) have one or more free amine groups, which can be reacted with dichloroacetyl chloride to make one or more trichloroacetyl amide groups. Upon hydrolysis, the prodrugs will hydrolyze in vivo to form dichloroacetic acid salts ("DCA") and the triphenylmethane compounds, both of which are useful in treating cancer. That is, DCA has been tested on in vitro cancer cell lines and a rat model, and found to restore mitochondrial function, thus restoring apoptosis, killing cancer cells in vitro, and shrinking the tumors in the rats. (See Bonnet et al., Cancer Cell 11 (1): 37-51 (2007).

For example, the prodrugs can be prepared by reacting quaternary ammonium groups with a reducing agent such as sodium cyanoborohydride to form amines. The amines can be reoxidized in vivo, particularly when taken up into cancer cells which product reactive oxygen species.

As discussed above, the amine groups can be converted to amide groups, which, upon hydrolysis, yield the amines, which can be oxidized to form the active compounds. Where the amide group is a trichloroacetyl amide group, the hydrolysis also produces the trichloroacetate salt, which can fight cancer via a different route than the active compounds (thus forming an in-situ drug cocktail from a single prodrug. Conditions for forming amides from amines and acids, or acid halides/anhydrides, are well known to those of skill in the art and need not be repeated here.

II. Methods of Preparing the Compounds

In some embodiments, the compounds can be prepared by reacting a diaryl ketone with a phenol or aniline compound, in the presence of a Lewis acid or phosphorus oxychloride or thionyl chloride. Using this approach, numerous triphenyl methanes can be made from readily available diaryl ketones and phenol or aniline starting materials. The reaction proceeds by electrophilic addition of the ketone moiety in the diaryl ketones to the ortho or para position of the aniline or phenol, followed by dehydration to form the triphenyl methanes.

As discussed below, routine chemistry can be used to prepare the diaryl ketones.

Methods of Forming Diaryl Ketones

The diaryl ketones used in the coupling step with phenols or anilines can either be commercially available, such as Michler's ketone, or can be prepared using known chemistry, or variations of known chemistry. Ideally, the aryl rings are functionalized in a manner that facilitates electrophilic aromatic substitution reactions (i.e., include electron donating substituents such as hydroxy, ether, thiol, thiolether, and amine).

Yun et al., Tetrahedron Letters, Volume 42, Issue 2, Pages 175-177 (8 Jan. 2001), discloses using a three-component Stille coupling reaction on solid phase to prepare diaryl ketones bearing a wide variety of functional groups. The reaction involves using a polymer-bound organostannane and aryl halides in the presence of carbon monoxide.

Silbestri et al. discloses the synthesis of a series of diaryl ketones, in good yields (40-78%), through the catalyst-free reaction of trimethylarylstannanes with aroyl chlorides in chlorobenzene as solvent (Silbestri et al., Journal of Organometallic Chemistry, Volume 691, Issue 8, Pages 1520-1524 (1 Apr. 2006)). These reactions are completely regioselective, making possible the synthesis of diarylketones which are not usually available under the influence of the directing forces of the substituents present in the aromatic ring. Also, the reaction conditions are mild enough to be applied to acid sensitive molecules.

Duplais et al. (Angewandte Chemie International Edition, Volume 43, Issue 22, Pages 2968-2970 (May 2004)) discloses the efficient synthesis of diaryl ketones by iron-catalyzed arylation of aroyl cyanides.

Enquist et al., Org. Lett., 5 (25), 4875-4878, 2003. 10.1021/ol036091x S1523-7060(03)06091-7 (Nov. 20, 2003), discloses the ultrafast synthesis of diaryl ketones using cobalt carbonyl-mediated synthesis under microwave irradiation The Enquist synthesis combined the advantages of metal activation, in situ carbon monoxide delivery, and microwave heating to efficiently synthesize benzophenones in 6-10 seconds. These ultrafast carbonylation reactions occur under air by flash heating of aryl iodides in the presence of dicobalt octacarbonyl. Thus, using suitably functionalized aryl iodides, one can rapidly prepare desired diaryl ketones.

Any of these reactions can be used to prepare the diaryl ketones described herein.

Triarylmethane Formation

Examples of the synthesis are shown below in Scheme I (where the asterisks show the respective ortho and para positions on the anilines and phenols where the electrophilic aromatic addition takes place, and the values for X and J are those described above with respect to Formulas 1-4):

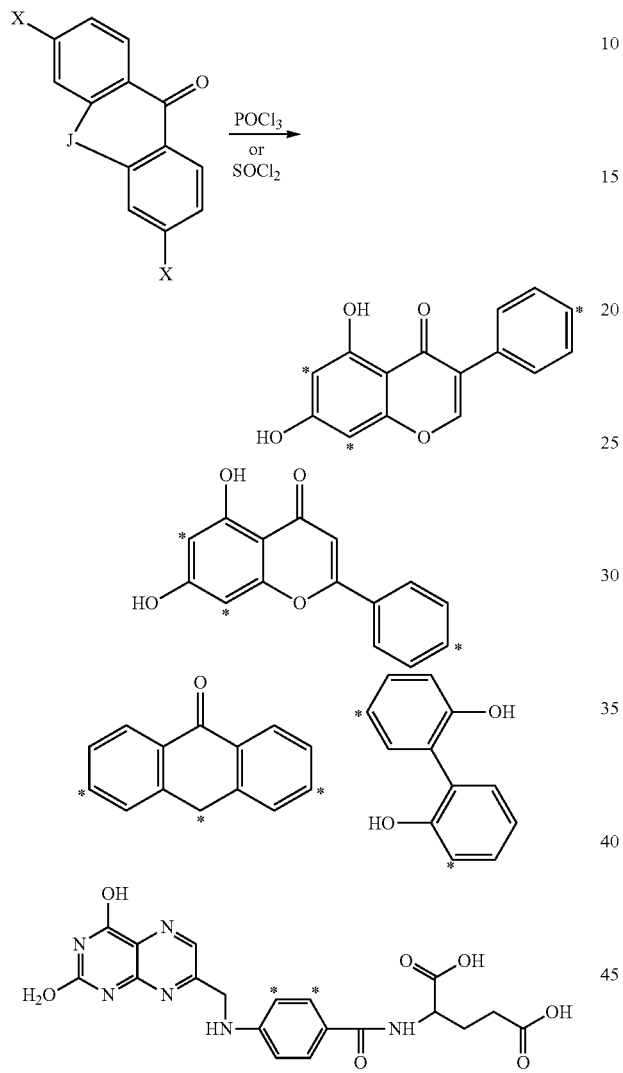

Formulas 1-4 show various aryl and heteroaryl rings, and these formulas are defined as including the possibility that the rings can be further functionalized with additional rings (either by direct coupling, as in naphthyl, or by a covalent linkage, as in biphenyl and other biaryl rings).

Representative aryl and heteroaryl rings that can be part of the diaryl ketones, phenols, and anilines are provided below (with the understanding that the rings will include appropriate aryl ketone, hydroxy, or amine functionalization):

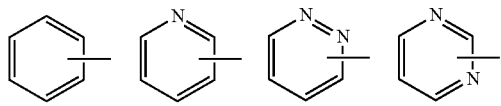

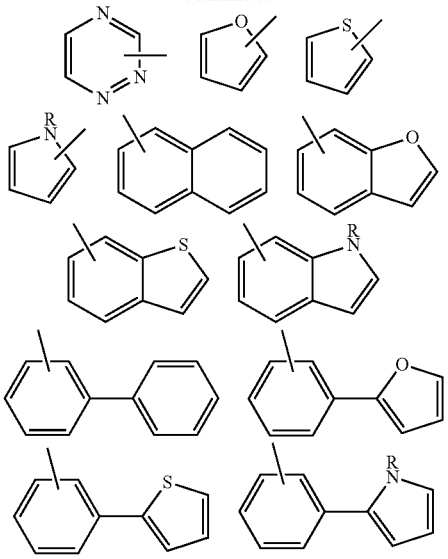

wherein any of the aryl/heteroaryl rings can be substituted with one or more substituents as described herein.

Functionalization of the Diaryl Ketones, Phenols and Anilines

The diaryl ketones, phenols, and anilines used to make compounds described herein are either commercially available, or can be prepared from commercially available starting materials. Those that are not commercially available can be made by a variety of synthetic methodologies, related to the particular moieties and the particular substitution desired. The variation in synthetic methodology will be readily apparent to those of skill in the art of organic synthesis.

Those skilled in the art will readily understand that incorporation of other substituents onto the aryl or heteroaryl rings used as a starting material to prepare the triarylmethanes, and other positions in the triarylmethane framework, can be readily realized. Also, various substituents can be added after the triarylmethanes have been prepared. Such substituents can provide useful properties in and of themselves or serve as a handle for further synthetic elaboration.

Substituents typically can be added to a diaryl ketone before reaction with the phenol or aniline, or to the aryl ring before preparation of the diaryl ketone, as discussed above. One proviso is that such substitution should either survive the triarylmethane synthesis by coupling the diaryl ketone and the phenol or aniline (i.e., Lewis Acid conditions), or should be added after the triarylmethane synthesis is complete.

For example, aryl rings can be halogenated using various known procedures, which vary depending on the particular halogen. Examples of suitable reagents include bromine/water in concentrated HBr, thionyl chloride, pyr-ICl, fluorine and Amberlyst-A. A number of other analogs, bearing substituents in a diazotized position of an aryl ring, can be synthesized from the corresponding aniline compounds, via the diazonium salt intermediate. The diazonium salt intermediates can be prepared using known chemistry, for example, treatment of aromatic amines such as aniline with sodium nitrite in the presence of a mineral acid.

Diazonium salts can be formed from anilines, which in turn can be prepared from nitrobenzenes (and analogous amine-substituted heteroaryl rings can be prepared from nitro-substituted heteroaryl rings). The nitro derivatives can be reduced to the amine compound by reaction with a nitrite salt, typically in the presence of an acid. Other substituted analogs can be produced from diazonium salt intermediates, including, but are not limited to, hydroxy, alkoxy, fluoro, chloro, iodo, cyano, and mercapto, using general techniques known to those of skill in the art. For example, hydroxy-triphenyl methane analogues can be prepared by reacting the diazonium salt intermediate with water, protecting the resulting hydroxyl group, forming the cyclopentadienyl anion, and reacting it with a suitable aldehyde or ketone. Likewise, alkoxy triphenyl methane analogues can be made by reacting the diazonium salt with alcohols. The diazonium salt can also be used to synthesize cyano or halo compounds, as will be known to those skilled in the art. Mercapto substitutions can be obtained using techniques described in Hoffman et al., *J. Med. Chem.* 36: 953 (1993). The mercaptan so generated can, in turn, be converted to an alkylthio substitutent by reaction with sodium hydride and an appropriate alkyl bromide. Subsequent oxidation would then provide a sulfone. Acylamido analogs of the aforementioned compounds can be prepared by reacting the corresponding amino compounds with an appropriate acid anhydride or acid chloride using techniques known to those skilled in the art of organic synthesis.

Hydroxy-substituted analogs can be used to prepare corresponding alkanoyloxy-substituted compounds by reaction with the appropriate acid, acid chloride, or acid anhydride. Likewise, the hydroxy compounds are precursors of both the aryloxy and heteroaryloxy via nucleophilic aromatic substitution at electron deficient aromatic rings. Such chemistry is well known to those skilled in the art of organic synthesis. Ether derivatives can also be prepared from the hydroxy compounds by alkylation with alkyl halides and a suitable base or via Mitsunobu chemistry, in which a trialkyl- or triarylphosphine and diethyl azodicarboxylate are typically used. See Hughes, *Org. React.* (N.Y.) 42: 335 (1992) and Hughes, *Org. Prep. Proced. Int.* 28: 127 (1996) for typical Mitsunobu conditions.

Cyano-substituted analogs can be hydrolyzed to afford the corresponding carboxamido-substituted compounds. Further hydrolysis results in formation of the corresponding carboxylic acid-substituted analogs. Reduction of the cyano-substituted analogs with lithium aluminum hydride yields the corresponding aminomethyl analogs. Acyl-substituted analogs can be prepared from corresponding carboxylic acid-substituted analogs by reaction with an appropriate alkyllithium using techniques known to those skilled in the art of organic synthesis.

Carboxylic acid-substituted analogs can be converted to the corresponding esters by reaction with an appropriate alcohol and acid catalyst. Compounds with an ester group can be reduced with sodium borohydride or lithium aluminum hydride to produce the corresponding hydroxymethyl-substituted analogs. These analogs in turn can be converted to compounds bearing an ether moiety by reaction with sodium hydride and an appropriate alkyl halide, using conventional techniques. Alternatively, the hydroxymethyl-substituted analogs can be reacted with tosyl chloride to provide the corresponding tosyloxymethyl analogs, which can be converted to the corresponding alkylamninoacyl analogs by sequential treatment with thionyl chloride and an appropriate alkylamine. Certain of these amides are known to readily undergo nucleophilic acyl substitution to produce ketones.

Hydroxy-substituted analogs can be used to prepare N-alkyl- or N-arylcarbamoyloxy-substituted compounds by reaction with N-alkyl- or N-arylisocyanates. Amino-substituted analogs can be used to prepare alkoxycarboxamido-substituted compounds and urea derivatives by reaction with alkyl chloroformate esters and N-alkyl- or N-arylisocyanates, respectively, using techniques known to those skilled in the art of organic synthesis.

Similarly, benzene rings (and pyridine, pyrimidine, pyrazine, and other heteroaryl rings) can be substituted using known chemistry, including the reactions discussed above. For example, the nitro group on nitrobenzene can be reacted with sodium nitrite to form the diazonium salt, and the diazonium salt manipulated as discussed above to form the various substituents on a benzene ring.

Synthesis of Imipramine Blue

One novel compound which was tested in several of the examples described herein has been named "imipramine blue." Imipramine blue has the following formula:

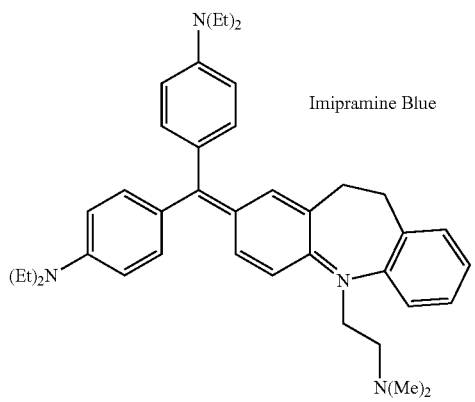

Imipramine Blue

Imipramine blue can be synthesized by reacting imipramine with Mischler's Ketone and an acid like phosphorus oxychloride ($POCl_3$), as shown below:

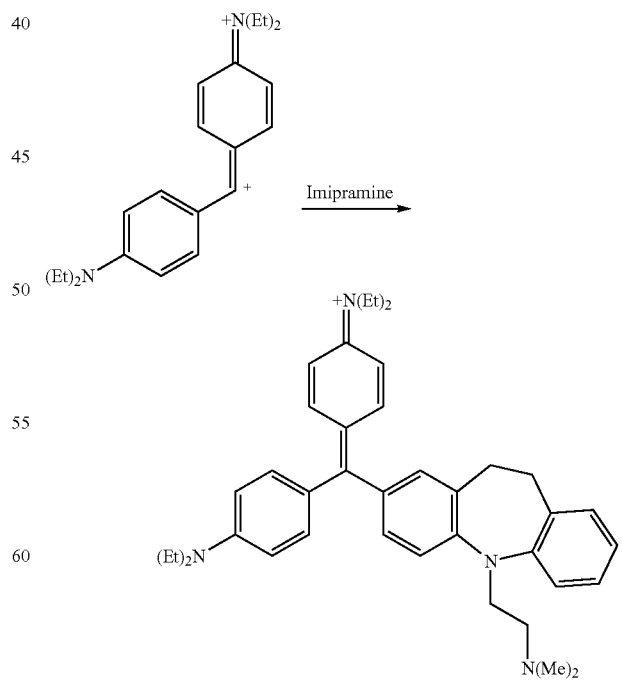

Other compounds described herein can be prepared using a similar synthetic method.

III. Pharmaceutical Compositions

The compounds described herein can be incorporated into pharmaceutical compositions and used to prevent a condition or disorder in a subject susceptible to such a condition or disorder, and/or to treat a subject suffering from the condition or disorder. The pharmaceutical compositions described herein include one or more of the triphenyl methane analogues described herein, and/or pharmaceutically acceptable salts thereof. Optically active compounds can be employed as racemic mixtures, as pure enantiomers, or as compounds of varying enantiomeric purity.

The manner in which the compounds are administered can vary. The compositions are preferably administered orally (e.g., in liquid form within a solvent such as an aqueous or non-aqueous liquid, or within a solid carrier). Preferred compositions for oral administration include pills, tablets, capsules, caplets, syrups, and solutions, including hard gelatin capsules and time-release capsules. Compositions may be formulated in unit dose form, or in multiple or subunit doses. Preferred compositions are in liquid or semisolid form. Compositions including a liquid pharmaceutically inert carrier such as water or other pharmaceutically compatible liquids or semisolids may be used. The use of such liquids and semisolids is well known to those of skill in the art.

The compositions can also be administered via injection, i.e., intraveneously, intramuscularly, subcutaneously, intraperitoneally, intraarterially, intrathecally; intravitreally, subconjunctivally, periocularly and intracerebroventricularly. Intravenous administration is a preferred method of injection. Suitable carriers for injection are well known to those of skill in the art, and include 5% dextrose solutions, saline, and phosphate buffered saline. The compounds can also be administered as an infusion or injection (e.g., as a suspension or as an emulsion in a pharmaceutically acceptable liquid or mixture of liquids).

The formulations may also be administered using other means, for example, rectal administration. Formulations useful for rectal administration, such as suppositories, are well known to those of skill in the art. The compounds can also be administered by inhalation (e.g., in the form of an aerosol either nasally or using delivery articles of the type set forth in U.S. Pat. No. 4,922,901 to Brooks et al., the disclosure of which is incorporated herein in its entirety); topically (e.g., in lotion form); or transdermally (e.g., using a transdermal patch, using technology that is commercially available from Novartis and Alza Corporation). Although it is possible to administer the compounds in the form of a bulk active chemical, it is preferred to present each compound in the form of a pharmaceutical composition or formulation for efficient and effective administration.

The compounds can be incorporated into drug delivery devices such as nanoparticles, microparticles, microcapsules, and the like. Representative microparticles/nanoparticles include those prepared with cyclodextrins, such as pegylated cyclodextrins, liposomes, including small unilamellar vesicles, and liposomes of a size designed to lodge in capillary beds around growing tumors. Suitable drug delivery devices are described, for example, in Heidel J D, et al., Administration in non-human primates of escalating intravenous doses of targeted nanoparticles containing ribonucleotide reductase subunit M2 siRNA, Proc Natl Acad Sci USA. 2007 Apr. 3; 104(14):5715-21; Wongmekiat et al., Preparation of drug nanoparticles by co-grinding with cyclodextrin: formation mechanism and factors affecting nanoparticle formation, Chem Pharm Bull (Tokyo). 2007 March; 55(3):359-63; Bartlett and Davis, Physicochemical and biological characterization of targeted, nucleic acid-containing nanoparticles. Bioconjug Chem. 2007 March-April; 18(2): 456-68; Villalonga et al., Amperometric biosensor for xanthine with supramolecular architecture, Chem. Commun. (Camb). 2007 Mar. 7; (9):942-4; Defaye et al., Pharmaceutical use of cyclodextrines: perspectives for drug targeting and control of membrane interactions, Ann Pharm Fr. 2007 January; 65(1):33-49; Wang et al., Synthesis of Oligo(ethylenediamino)-beta-Cyclodextrin Modified Gold Nanoparticle as a DNA Concentrator; Mol Pharm. 2007 March-April; 4(2): 189-98; Xia et al., Controlled synthesis of Y-junction polyaniline nanorods and nanotubes using in situ self-assembly of magnetic nanoparticles, J Nanosci Nanotechnol., 2006 December; 6(12):3950-4; and Nijhuis et al., Room-temperature single-electron tunneling in dendrimer-stabilized gold nanoparticles anchored at a molecular printboard, Small. 2006 December; 2(12):1422-6.

Exemplary methods for administering such compounds will be apparent to the skilled artisan. The usefulness of these formulations may depend on the particular composition used and the particular subject receiving the treatment. These formulations may contain a liquid carrier that may be oily, aqueous, emulsified or contain certain solvents suitable to the mode of administration.

The compositions can be administered intermittently or at a gradual, continuous, constant or controlled rate to a warm-blooded animal (e.g., a mammal such as a mouse, rat, cat, rabbit, dog, pig, cow, or monkey), but advantageously are administered to a human being. In addition, the time of day and the number of times per day that the pharmaceutical formulation is administered can vary.

Preferably, the compositions are administered such that active ingredients interact with regions where cancer cells are located. The compounds described herein are very potent at treating these cancers.

In certain circumstances, the compounds described herein can be employed as part of a pharmaceutical composition with other compounds intended to prevent or treat a particular cancer, i.e., combination therapy. In addition to effective amounts of the compounds described herein, the pharmaceutical compositions can also include various other components as additives or adjuncts.

Complexation with Proteins

The compounds described herein can be complexed with peptides and proteins, including albumin, transferrin, VEGF, bFGF, and the like. These complexes are easy to make and tend to have lower toxicity than the un-complexed compounds.

When administered, it is believed that the triphenylmethanes are highly protein bound. One can create novel delivery forms by taking advantage of this binding, in that aqueous solutions of triphenylmethane can be incubated with specific proteins that can target leaky vessels (ie albumin) or proteins that target the tumor or its vasculature (VEGF, transferrin, collagen type 7, insulin like growth factor, PDGF, etc). Once the triphenylmethane has formed a complex with the protein, it can be infused, for example, intraveneously, intramuscularly, and/or subcutaneously, and the protein complex binds to the receptor, is internalized, and the triphenylmethane is released in the target cell.

Combination Therapy

The combination therapy may be administered as (a) a single pharmaceutical composition which comprises a triphenyl methane analogue as described herein, at least one additional pharmaceutical agent described herein, and a pharmaceutically acceptable excipient, diluent, or carrier; or (b) two separate pharmaceutical compositions comprising (i) a first composition comprising a triphenyl methane analogue as described herein and a pharmaceutically acceptable excipient, diluent, or carrier, and (ii) a second composition comprising at least one additional pharmaceutical agent described herein and a pharmaceutically acceptable excipient, diluent, or carrier. The pharmaceutical compositions can be administered simultaneously or sequentially and in any order.

In use in treating or preventing cancer, the triphenyl methane analogues described herein can be administered together with at least one other chemotherapeutic agent as part of a unitary pharmaceutical composition. Alternatively, the triphenyl methane analogues can be administered apart from the other anticancer chemotherapeutic agent. In this embodiment, the triphenyl methane analogues and the at least one other anticancer chemotherapeutic agent are administered substantially simultaneously, i.e. the compounds are administered at the same time or one after the other, so long as the compounds reach therapeutic levels for a period of time in the blood.

Combination therapy involves administering a triphenyl methane analogue, as described herein, or a pharmaceutically acceptable salt or prodnrug of a compound described herein, in combination with at least one anti-cancer chemotherapeutic agent, ideally one which functions by a different mechanism (i.e., VEGF inhibitors, alkylating agents, and the like).

Examples of known anticancer agents which can be used for combination therapy include, but are not limited to alkylating agents, such as busulfan, cis-platin, mitomycin C, and carboplatin; antimitotic agents, such as colchicine, vinblastine, paclitaxel, and docetaxel; topo I inhibitors, such as camptothecin and topotecan; topo II inhibitors, such as doxorubicin and etoposide; RNA/DNA antimetabolites, such as 5-azacytidine, 5-fluorouracil and methotrexate; DNA antimetabolites, such as 5-fluoro-2'-deoxy-uridine, ara-C, hydroxyurea and thioguanine; and antibodies, such as Herceptin® and Rituxan®. Other known anti-cancer agents, which can be used for combination therapy, include arsenic trioxide, gamcitabine, melphalan, chlorambucil, cyclophosamide, ifosfamide, vincristine, mitoguazone, epirubicin, aclarubicin, bleomycin, mitoxantrone, elliptinium, fludarabine, octreotide, retinoic acid, tamoxifen and alanosine. Other classes of anti-cancer compounds that can be used in combination with the triphenyl methane analogues are described below.

The triphenyl methane analogues can be combined with alpha-1-adrenoceptor antagonists, such as doxazosin, terazosin, and tamsulosin, which can inhibit the growth of prostate cancer cell via induction of apoptosis (Kyprianou, N., et al., Cancer Res 60:4550 4555, (2000)).

Sigma-2 receptors are expressed in high densities in a variety of tumor cell types (Vilner, B. J., et al., Cancer Res. 55: 408 413 (1995)) and sigma-2 receptor agonists, such as CB-64D, CB-184 and haloperidol, activate a novel apoptotic pathway and potentiate antineoplastic drugs in breast tumor cell lines. (Kyprianou, N., et al., Cancer Res. 62:313 322 (2002)). Accordingly, the triphenyl methane analogues can be combined with at least one known sigma-2 receptor agonists, or a pharmaceutically acceptable salt of said agent.

The triphenyl methane analogues can be combined with lovastatin, a HMG-CoA reductase inhibitor, and butyrate, an inducer of apoptosis in the Lewis lung carcinoma model in mice, can potentiate antitumor effects (Giermasz. A., et al., Int. J. Cancer 97:746 750 (2002)). Examples of known HMG-CoA reductase inhibitors, which can be used for combination therapy include, but are not limited to, lovastatin, simvastatin, pravastatin, fluvastatin, atorvastatin and cerivastatin, and pharmaceutically acceptable salts thereof.

Certain HIV protease inhibitors, such as indinavir or saquinavir, have potent anti-angiogenic activities and promote regression of Kaposi sarcoma (Sgadari, C., et al., Nat. Med. 8:225 232 (2002)). Accordingly (in addition to forming triphenyl methane analogues of these compounds), the triphenyl methane analogues can be combined with HIV protease inhibitors, or a pharmaceutically acceptable salt of said agent. Representative HIV protease inhibitors include, but are not limited to, amprenavir, abacavir, CGP-73547, CGP-61755, DMP-450, indinavir, nelfinavir, tipranavir, ritonavir, saquinavir, ABT-378, AG 1776, and BMS-232,632.

Synthetic retinoids, such as fenretinide (N-(4-hydroxyphenyl)retinamide, 4HPR), can have good activity in combination with other chemotherapeutic agents, such as cisplatin, etoposide or paclitaxel in small-cell lung cancer cell lines (Kalemkerian, G. P., et al., Cancer Chemother. Pharmacol. 43:145 150 (1999)). 4HPR also was reported to have good activity in combination with gamma-radiation on bladder cancer cell lines (Zou, C., et al., Int. J. Oncol. 13:1037 1041 (1998)). Representative retinoids and synthetic retinoids include, but are not limited to, bexarotene, tretinoin, 13-cis-retinoic acid, 9-cis-retinoic acid, .alpha.-difluoromethylornithine, ILX23-7553, fenretinide, and N-4-carboxyphenyl retinamide.

Proteasome inhibitors, such as lactacystin, exert antitumor activity in vivo and in tumor cells in vitro, including those resistant to conventional chemotherapeutic agents. By inhibiting NF-kappaB transcriptional activity, proteasome inhibitors may also prevent angiogenesis and metastasis in vivo and further increase the sensitivity of cancer cells to apoptosis (Almond, J. B., et al., Leukemia 16:433 443 (2002)). Representative proteasome inhibitors include, but are not limited to, lactacystin, MG-132, and PS-341.

Tyrosine kinase inhibitors, such as STI571 (Imatinib mesilate, Gleevec®), have potent synergetic effects in combination with other anti-leukemic agents, such as etoposide (Liu, W. M., et al. Br. J. Cancer 86:1472 1478 (2002)). Representative tyrosine kinase inhibitors include, but are not limited to, Gleevec®, ZD1839 (Iressa®). SH268, genistein, CEP2563, SU6668, SU11248, and EMD121974.

Prenyl-protein transferase inhibitors, such as farnesyl protein transferase inhibitor R115777, possess antitumor activity against human breast cancer (Kelland, L. R., et. al., Clin. Cancer Res. 7:3544 3550 (2001)). Synergy of the protein farnesyltransferase inhibitor SCH66336 and cisplatin in human cancer cell lines also has been reported (Adjei, A. A., et al., Clin. Cancer. Res. 7:1438 1445 (2001)). Prenyl-protein transferase inhibitors, including farnesyl protein transferase inhibitor, inhibitors of geranylgeranyl-protein transferase type I (GGPTase-T) and geranylgeranyl-protein transferase type-H, or a pharmaceutically acceptable salt of said agent, can be used in combination with the triphenyl methane analogues described herein. Examples of known prenylprotein transferase inhibitors include, but are not limited to, R115777, SCH66336, L-778,123, BAL9611 and TAN-1813.

Cyclin-dependent kinase (CDK) inhibitors, such as flavopiridol, have potent, often synergetic, effects in combination with other anticancer agents, such as CPT-11, a DNA topoisomerase I inhibitor in human colon cancer cells (Motwani, M., et al., Clin. Cancer Res. 7:4209 4219, (2001)). Representative cyclin-dependent kinase inhibitors include, but are not limited to, flavopiridol, UCN-01, roscovitine and olomoucine.

Certain COX-2 inhibitors are known to block angiogenesis, suppress solid tumor metastases, and slow the growth of implanted gastrointestinal cancer cells (Blanke, C. D., Oncology (Hunting) 16(No. 4 Suppl. 3):17 21 (2002)). Representative COX-2 inhibitors include, but are not limited to, celecoxib, valecoxib, and rofecoxib.

IκB-α phosphorylation inhibitors, such as BAY-11-7082 (an irreversible inhibitor of IκB-α phosphorylation) are also known to induce apoptosis, or to enhance the effectiveness of other agents at inducing apoptosis. These inhibitors can also be used in combination with the compounds described herein.

Any of the above-mentioned compounds can be used in combination therapy with the triphenyl methane analogues. Additionally, many of these compounds can be converted to triphenyl methane analogues by reaction of ketone, aldehyde, hydroxyl, thiol, and/or amine functional groups on the compounds using the chemistry described herein. The triphenyl methane analogues of these compounds are within the scope of this invention.

Further, the triphenyl methane analogues can be targeted to a tumor site by conjugation with therapeutically useful antibodies, such as Herceptin® or Rituxan®, growth factors, such as DGF, NGF; cytokines, such as IL-2, IL-4, or any molecule that binds to the cell surface. The antibodies and other molecules will deliver a compound described herein to its targets and make it an effective anticancer agent. The bioconjugates can also enhance the anticancer effect of therapeutically useful antibodies, such as Herceptin® or Rituxan®.

The compounds can also be used in conjunction with surgical tumor removal, by administering the compounds before and/or after surgery, and in conjunction with radiation therapy, by administering the compounds before, during, and/or after radiation therapy.

The appropriate dose of the compound is that amount effective to prevent occurrence of the symptoms of the disorder or to treat some symptoms of the disorder from which the patient suffers. By "effective amount", "therapeutic amount" or "effective dose" is meant that amount sufficient to elicit the desired pharmacological or therapeutic effects, thus resulting in effective prevention or treatment of the disorder.

When treating cancers, an effective amount of the triphenyl methane analogue is an amount sufficient to suppress the growth of the tumor(s), and, ideally, is a sufficient amount to shrink the tumor, and, more ideally, to destroy the tumor. Cancer can be prevented, either initially, or from re-occurring, by administering the compounds described herein in a prophylactic manner. Preferably, the effective amount is sufficient to obtain the desired result, but insufficient to cause appreciable side effects.

The effective dose can vary, depending upon factors such as the condition of the patient, the severity of the cancer, and the manner in which the pharmaceutical composition is administered. The effective dose of compounds will of course differ from patient to patient, but in general includes amounts starting where desired therapeutic effects occur but below the amount where significant side effects are observed.

The compounds, when employed in effective amounts in accordance with the method described herein, are selective to certain cancer cells, but do not significantly affect normal cells.

For human patients, the effective dose of typical compounds generally requires administering the compound in an amount of at least about 1, often at least about 10, and frequently at least about 25 μg/24 hr/patient. The effective dose generally does not exceed about 500, often does not exceed about 400, and frequently does not exceed about 300 μg/24 hr/patient. In addition, administration of the effective dose is such that the concentration of the compound within the plasma of the patient normally does not exceed 500 ng/mL and frequently does not exceed 100 ng/mL.

IV. Methods of Using the Compounds and/or Pharmaceutical Compositions

The compounds described herein, and pharmaceutical compositions including the compounds, can be used to treat cancers. The cancers include those in which one of the Nox enzymes is present in elevated concentrations (i.e., Nox 1, Nox 4, and the like), or those in which cancer growth is mediated by ROS.

Representative disorders that can be treated include neoplasms, such as hemangiomas, and malignant tumors, for example, those which arise in the setting of autocrine loops involving vascular endothelial growth factor (VEGF) and its major mitogenic receptor vascular endothelial growth factor receptor 2. Representative malignant tumors include malignant endothelial tumors such as melanoma.

Representative malignant tumors include malignant endothelial tumors such as melanoma. Additional cancers that can be treated include, but not limited to human sarcomas and carcinomas, e.g., fibrosarcoma, myxosarcoma, liposarcoma, chondrosarcoma, osteogenic sarcoma, chordoma, angiosarcoma, endotheliosarcoma, lymphangiosarcoma, lymphangioendotheliosarcoma, synovioma, mesothelioma. Ewing's tumor, leiomyosarcoma, rhabdomyosarcoma, colon carcinoma, pancreatic cancer, breast cancer, ovarian cancer, prostate cancer, squamous cell carcinoma, basal cell carcinoma, adenocarcinoma, sweat gland carcinoma, sebaceous gland carcinoma, papillary carcinoma, papillary adenocarcinomas, cystadenocarcinoma, medullary carcinoma, bronchogenic carcinoma, renal cell carcinoma, hepatoma, bile duct carcinoma, choriocarcinoma, seminoma, embryonal carcinoma, Wilms' tumor, cervical cancer, testicular tumor, lung carcinoma, small cell lung carcinoma, bladder carcinoma, epithelial carcinoma, glioma, astrocytoma, medulloblastoma, craniopharyngioma, ependymoma, pinealoma, hemangioblastoma, acoustic neuroma, oligodendroglioma, meningioma, melanoma, neuroblastoma, retinoblastoma; leukemias, e.g., plasma cell leukemia, acute lymphocytic leukemia, acute myelocytic leukemia (myeloblastic, promyelocytic, myelomonocytic, monocytic and erythroleukemia); chronic leukemia (chronic myelocytic (granulocytic) leukemia and chronic lymphocytic leukemia); and polycythemia vera, lymphoma (Hodgkin's disease and non-Hodgkin's disease), including NF-KB mutant and Velcade Resistant lymphoma cells, multiple myeloma, PI3 kinase deficient myeloma. Waldenstrom's macroglobulinemia, and heavy chain disease, and malignant forms of these cancers. Additionally, the compounds can be used in assays involving lymphoblastoid and EBV positive cells.

In one embodiment, the cancer is melanoma, rectal carcinoma, colon carcinoma, breast carcinoma, ovarian carcinoma, small cell lung carcinoma, colon carcinoma, chronic lymphocytic carcinoma, hairy cell leukemia, esophogeal carcinoma, prostate carcinoma, breast cancer, myeloma, or lymphoma. It is believed that these cancers have circulating levels of tNOX (which may include Nox4 or other Nox enzymes) present in the sera of patients suffering from the cancer (see, for example, U.S. Pat. No. 5,605,810, which is hereby incorporated by reference in its entirety).

In some embodiments, the patient already has cancer and is undergoing treatment for the cancer, and may or may not have tumor metastasis (i.e., secondary cancer).

In other embodiments, the compounds are active at inhibiting hypoxia-inducible factor HIF2a expression, and this activity aids in the treatment of tumors resistant to standard chemoradiotherapy. Hypoxia-inducible factor HIF2alpha (HIFalphas) regulates the expression of a variety of genes encoding proteins related to angiogenesis and to anaerobic metabolism of cells exposed to hypoxic stress (Koukourakis et al., Int J Radiat Oncol Biol Phys. 2002 Aug. 1; 53(5): 1192-202.) HIF2a overexpression is significantly associated with high microvessel density (p=0.02, respectively) and with VEGF expression (p=0.005), and VEGF/KDR-activated tumor vasculature is more frequent in HIF2a-overexpressing tumors (p=0.02). High HIF2a levels have been associated with incomplete response to chemoradiation (p=0.02, respectively), and overexpression of HIF2a is related to locally aggressive behavior, intensification of angiogenesis, and resistance to carboplatin chemoradiotherapy.

Imipramine blue was evaluated in a HIF2a expression model, and was shown to inhibit around 90% of the HIF2a expression. In this expression model, WM35 PKB cells are exposed to 5 micromolar of test compounds for 24 hours. At the end of this period, cells are harvested for RNA, which is then reverse transcribed into cDNA, and levels of HIF2a message are quantified using quantitative RT-PCR and corrected for a housekeeping RNA message. As demonstrated using this assay, these compounds can act as direct NADPH oxidase inhibitors, as well as superoxide scavengers that absorb superoxide produced by defective mitochondria or other cellular processes.

The cancer may be manifested in the form of a tumor, such as a tumor of epithelial tissue, lymphoid tissue, connective tissue, bone, or central nervous system.

The compounds can also be used as adjunct therapy in combination with existing therapies in the management of the aforementioned types of cancers. In such situations, it is preferably to administer the active ingredients to in a manner that optimizes effects upon cancer cells, including drug resistant cancer cells, while minimizing effects upon normal cell types. While this is primarily accomplished by virtue of the behavior of the compounds themselves, this can also be accomplished by targeted drug delivery and/or by adjusting the dosage such that a desired effect is obtained without meeting the threshold dosage required to achieve significant side effects.

Specific Disorders Mediated by $Nox_2$ and $Nox_4$ Receptors $Nox_2$ and $Nox_4$ are NADPH oxidases. $Nox_2$ exists as part of a multiprotein complex, known as cytochrome b558, which includes phox p47phox, p22phox and p21rac, as well as p67phox. Rac may be either rac1 or 2. $Nox_4$ may not require complexing with these proteins.

$Nox_2$ is highly expressed in neutrophils, macrophages and lymphocytes, and may mediate reactive oxygen driven NFkB in inflammatory and neoplastic processes involving neutrophils, macrophages, and lymphocytes, ie leukemias and lymphomas.

Nox4 is a widely distributed NADPH oxidase, which is highly expressed in many malignancies, ie melanoma, pancreatic cancer, etc, and generates reactive oxygen that drives NFkB, which then activates antiapoptotic genes such as bcl2 and mcl-1, resulting in resistance to radiation and chemotherapy.

It is proposed that blockade of superoxide will result in decreased expression of NFkB, and will sensitize malignancies to radiation and chemotherapy.

Disorders that are characterized by excess reactive oxygen can be classified into disorders which can be treated and prevented, and patients whose immune systems become more active following administration of the compounds described herein (i.e., immune potentiation). The following disorders can be treated using the compounds described herein:

a) Neoplastic-hemangiomas, melanoma, lung cancer, breast cancer, colon cancer, pancreatic cancer, prostate cancer, ovarian cancer, brain tumors including glioblastoma multiforme, sarcomas, head and neck cancers, hepatocellular carcinoma, nasopharyngeal carcinoma, cervical cancer and precancer, hematologic malignancies including multiple myeloma, myelodysplatic syndrome, acute and chronic leukemias, Hodgkins disease, non hodgkins lymphoma, including diffuse large B cell lymphoma (DLBCL)

b) Inflammatory disorders—psoriasis, atopic dermatitis (eczema), asthma, arthritis (including rheumatoid, psoriatic), inflammatory bowel disease (including Crohns and ulcerative colitis), lupus, multiple sclerosis, Sjogrens disease, gastritis and pernicious anemia, sprue, sarcoidosis, vitiligo, alopecia areata, scleroderma, fibrotic disorders, cirrhosis, coronary artery disease, atherosclerosis, myositis, myocarditis c) Degenerative disease—macular degeneration, Alzheimers disease, parkinsons disease, lewy body dementia, prion mediated disorders, emphysema, cataracts, photoaging of skin, pterygium, osteoporosis, pattern hair loss, hypertension, stroke D) Infectious disease-Bacterial, including Staph, i.e. MRSA, viral (i.e., herpes, HIV, HBV, HCV, HPV, and influenza), and fungal (i.e., *Candida*)

Treatment of Osteoporosis

The compounds described herein can also be used to treat osteoporosis. The cytokine RANKL (receptor activator of NF-κB ligand) causes osteoporosis by activating osteoclasts. The compounds inhibit RANKL activity by potentiating apoptosis, suppresses osteoclastogenesis, and inhibits invasion through modulation of nuclear factor-kappaB activation pathway (see, for example, Mol Cancer Res. 2006 September; 4(9):621-33).

Treatment of Inflammatory Disorders

The compounds described herein are useful for treating or preventing inflammatory disorders. Reactive oxygen drives NFkB in inflammatory disorders such as rheumatoid arthritis, asthma, psoriasis, excema, lupus, scleroderma, certain heart diseases such atherosclerosis and coronary artery disease, and the like. Because the compounds are effective at inhibiting production of reactive oxygen species, they are active against inflammatory disorders.

The compounds also inhibit certain inflammatory signals, and can alleviate inflammatory disorders such as inflammatory arthritis by inhibiting these signals.

Rheumatoid arthritis (RA) is considered the most common systemic autoimmune disease, but other disorders, such as hypothyroidism, systemic lupus erythematosus (SLE), and the like can also be treated using the compounds described herein. A number of conditions are associated with chronic inflammation and elevated levels of TNF-α and IL-6, including rheumatoid arthritis, heart disease, and cancer. Numerous gastrointestinal disorders are caused by inflammation, including, but not limited to, Crohn's disease, irritable bowel syndrome, and inflammatory bowel syndrome, and these disorders can also be treated and/or prevented using the compounds described herein.

There is a suggested link between rheumatoid arthritis and chronic inflammation due to the re-activation of Epstein-Barr virus (EBV), which latently infects a proportion of memory B cells in >90% of the world's population. Among the EBV-encoded proteins implicated in viral pathogenesis, considerable attention has focused upon latent membrane protein 1 (LMP1). Of the nine EBV genes expressed as proteins in EBV-transformed cells. LMP1 is the best characterized, and is the only EBV-encoded gene product capable of transforming cells in vitro and in vivo, resulting in the potential for lymphoproliferative changes and malignancy. In addition to its established role in the pathogenesis of B cell lymphoma and other malignancies, EBV infection may be linked to exacerbation of various human autoimmune diseases, including RA and SLE.

The mouse collagen-induced arthritis (CIA) model (Myers, et al., *Life Science* 61: 1861-1878 (1997)) has many pathologic and immunologic parallels to rheumatoid arthritis, and provides a stable, predictable model for evaluating the therapeutic potential of compounds for treating chronic inflammatory conditions. This model can be used, for example, to evaluate the ability of the compounds described herein to treat and/or prevent these disorders.

Treatment of mouse B cell lines with compounds described herein in vitro can be shown to recapitulate the cytokine profile seen in primary mouse B cells with a concomitant dose-dependent decrease in CD40 and LMP1-mediated NFkB and AP-1 activation. Those compounds which decrease CD40 and LMP1-mediated NFkB and AP-1 activation in a dose-dependent manner will be expected to have anti-inflammatory properties, potentially in both the cognitive phase of the immune response, as well as the effector phase, by inhibiting cytokines that lead to chronic inflammation and additional pathology.

Treatment of Ocular Disorders

The compounds are also suitable for use in treating ocular disorders with an inflammatory component, such as wet and dry age-related macular degeneration (AMD), diabetic retinopathy (DR), glaucoma, neovascular glaucoma, retinal vasculitis, uveitis, such as posterior uveitis, conjunctivitis, retinitis secondary to glaucoma, episcleritis, scleritis, optic neuritis, retrobulbar neuritis, ocular inflammation following ocular surgery, ocular inflammation resulting from physical eye trauma, cataract, ocular allergy and dry eye.

There are also a variety of ocular infestations caused by parasites like brucellosis. Since these compounds kill parasites, they can also address the uveitis that normally results. For example, toxocara infections can cause ocular larva migrans (OLM), an eye disease that can cause blindness. OLM occurs when a microscopic worm enters the eye; it may cause inflammation and formation of a scar on the retina. Cysticercosis is a parasitic infestation of different body organs by Cysticercosis cellulosae. Ocular manifestations of *malaria* and leishmaniasis are well documented and site threatening conditions. These and other ocular parasitic infections can be treated using the compounds described herein Current methods for ocular delivery include topical administration (eye drops or other suitable topical formulations for direct administration to the eye), subconjunctival injections, periocular injections, intravitreal injections, surgical implants, and systemic routes.

Particularly where systemic toxicity is of concern when the oral and intravenous routes of administration are used, intravitreal injections, periocular injections, and sustained-release implants can be used to achieve therapeutic levels of drugs in ocular tissues. Eye drops are useful in treating conditions affecting either the exterior surface of the eye or tissues in the front of the eye, and some formulations can penetrate to the back of the eye for treatment of retinal diseases.

Certain disorders affect tissues at the back of the eye, where treatment is difficult to deliver. In these embodiments, iontophoresis can be used to deliver the compounds described herein to the back of the eye. For example, the ocular iontophoresis system, OcuPhor™, can deliver drugs safely and noninvasively to the back of the eye (Iomed). Iontophoresis uses a small electrical current to transport ionized drugs into and through body tissues. Care must be taken not to use too high of a current density, which can damage eye tissues.

Iontophoresis typically involves using a drug applicator, a dispersive electrode, and an electronic iontophoresis dose controller. The drug applicator can be a small silicone shell that contains a conductive element, such as silver-silver chloride. A hydrogel pad can absorb the drug formulation. A small, flexible wire can connect the conductive element to the dose controller. The drug pad can be hydrated with a drug solution immediately before use, with the applicator is placed on the sclera of the eye under the lower eyelid. The eyelid holds the applicator in place during treatment. The drug dose and rate of administration can be controlled by programming and setting the electronic controller.

Treatment of Neurodegenerative Disorders and/or Providing Neuroprotection

Reactive oxygen species also induce inflammation and neurodegeneration. Inhibition of these species can also result in neuroprotection, including protection from further damage following an ischemic brain injury such as a stroke, or that caused from blunt trauma, and treatment or prevention of neurodegenerative disorders such as retinal degenerations. Alzheimer's disease, senile dementia, pre-senile dementia, Parkinsons disease, Fragile X syndrome, tuberous sclerosis, Huntington's Chorea, multiple sclerosis, and the like.

Reactive oxygen species also drive seizures, and the compounds may ameliorate seizures as well.

Treatment of Vascular Disorders

Vascular diseases such as erectile dysfunction and migraines in which ROS have been implicated may also respond to NADPH oxidase inhibitors. The compounds described herein can be used to treat these vascular diseases.

Atherosclerosis is one vascular disorder known to be treated with NADPH oxidase inhibitors (see, for example, U.S. Pat. No. 5,763,496). Accordingly, the compounds can be used to prevent atherosclerosis and/or inhibit the development of an atherosclerotic plaque.

Treatment of Parasitic Infections

Certain of the compounds described herein can be used to treat or prevent parasitic certain infections. Among those parasitic infections that can be treated include *malaria*, trypanosomiasis, and leishmaniasis.

*Malaria* is caused by protozoan parasites of the genus *Plasmodium*. There are four species of *Plasmodium*, *Plasmodium falciparum*, *Plasmodium vivax*, *Plasmodium ovale*, and *Plasmodium malaria*. *P. falciparum* is the most widespread and dangerous, and left untreated, it can lead to fatal cerebral *malaria*.

Leishmaniasis is a disease caused by protozoan parasites belonging to the genus *Leishmania*. The disease is transmitted by the bite of certain species of sand flies, including flies in the genus *Lutzomyia* in the New World and *Phlebotomus* in the Old World.

There are four main forms of leishmaniasis. Visceral leishmaniasis is the most serious form and potentially fatal if untreated. Cutaneous leishmaniasis is the most common form, and causes a sore at the bite site. The sore can heal in a few months to a year, leaving an unpleasant looking scar, but can also progress to any of the other three forms. Diffuse cutaneous leishmaniasis is a form that produces widespread skin lesions which resemble leprosy and is particularly difficult to treat. Mucocutaneous leishmaniasis begins with skin ulcers which spread, causing tissue damage to the nose and mouth.

Trypanosomiasis is a disorder caused by a parasite called a trypanosome, and is commonly known as sleeping sickness. The parasite is transmitted to humans through the bite of a tsetse fly. There are two forms of African sleeping sickness, caused by two different parasites. *Trypanosoma brucei gambiense* causes a chronic infection lasting years, and is largely found in western and central Africa. *Trypanosoma brucei rhodesiense* causes acute illness lasting several weeks, and is largely found in eastern and southern Africa. If untreated, trypanosomiasis causes tremendous suffering, and ultimately ends in death.

Certain of the compounds described herein are effective at treating one or more of these disorders.

The following examples are provided to illustrate the present invention, and should not be construed as limiting thereof. In these examples, all parts and percentages are by weight, unless otherwise noted. Reaction yields are reported in mole percentages.

EXAMPLES

The following examples are provided to illustrate the present invention and should not be construed as limiting the scope thereof. In these examples, all parts and percentages are by weight, unless otherwise noted. Reaction yields are reported in mole percentage.

Example 1: Spectrophotometric Assay of NADH Oxidase

NADH oxidase activity can be determined as the disappearance of NADH measured at 340 nm in a reaction mixture containing 25 mM Tris-Mes buffer (pH 7.2), 1 mM KCN, and 150 µM NADH at 37° C. Activity can be measured, for example, using a Hitachi U3210 spectrophotometer with stirring and continuous recording over two intervals of 5 min each. A millimolar extinction coefficient of 6.22 can be used to determine specific activity.

Example 2: Measuring Cell Growth

A mouse mammary tumor subpopulation line 4T1 arising from a BALB/cf C3H mouse can be grown in DME-10. Dulbecco's modified Eagle's medium supplemented with 5% fetal calf serum, 5% newborn calf serum, 1 mM mixed non-essential amino acids, 2 mM L-glutamine, penicillin (100 units/ml), and streptomycin (100 µg/ml) (Miller et al., 1987, Brit. J. Can. 56:561-569 and Miller et al., 1990, Invasion Metastasis 10:101-112).

Example 3: Pharmacologic Blockade of Angiopoietin-2 is Efficacious Against Model Hemangiomas in Mice Hemangioma of infancy is the most common neoplasm of childhood. While hemangiomas are classic examples of angiogenesis, the angiogenic factors responsible for hemangiomas are not fully understood. Malignant endothelial tumors arise in the setting of autocrine loops involving vascular endothelial growth factor (VEGF) and its major mitogenic receptor vascular endothelial growth factor receptor 2.

Hemangiomas of infancy differ from malignant endothelial tumors in that they usually regress, or can be induced to regress by pharmacologic means, suggesting that angiogenesis in hemangiomas differs fundamentally from that of malignant endothelial tumors.

The data in this example demonstrate constitutive activation of the endothelial tie-2 receptor in human hemangioma of infancy and, using a murine model of hemangioma, bEnd.3 cells. bEnd.3 hemangiomas produce both angiopoietin-2 (ang-2) and its receptor, tie-2, in vivo. Inhibition of tie-2 signaling with a soluble tie-2 receptor decreases bEnd.3 hemangioma growth in vivo. The efficacy of tie-2 blockade suggests that either tie-2 activation or ang-2 may be required for in vivo growth.

To address this issue, tie-2-deficient bEnd.3 hemangioma cells were used. Surprisingly, these cells were fully proficient in in vivo growth. Previous studies from our laboratory and others have implicated reactive oxygen-generating nox enzymes in the angiogenic switch, so the effect of nox inhibitors was evaluated on ang-2 production in vitro and on bEnd.3 tumor growth in vivo. Ang-2 production was inhibited pharmacologically using novel inhibitors of nox enzymes, and this treatment nearly abolished bEnd.3 hemangioma growth in vivo. Signal-transduction blockade targeting ang-2 production may therefore be useful in the treatment of human hemangiomas in vivo.

The following abbreviations are used throughout this example:

Ang, angiopoietin;
DPI, diphenyliodonium:
VEGF, vascular endothelial growth factor
Introduction Hemangiomas are the most common tumor of infancy and childhood and account for a disproportionate number of visits to pediatricians and dermatologists (Chiller et al., 2003). Histologically, hemangiomas consist of clusters of endothelial cells surrounding vascular lumens of varying diameter. The natural history of hemangiomas begins with a proliferative phase, characterized by rapid growth of the tumor and endothelial division, followed by an imnoluting-stage, which is marked by endothelial apoptosis and decreasing tumor size, and finally ends with an imoluted stage, during which the original tumor is replaced by a connective tissue scar (Takahashi et al., 1994). While these tumors usually resolve spontaneously, large tumors can compromise the function of vital organs by compression, and may even lead to high-output cardiac failure (Drolet et al., 1999).

Studies have established the clonal nature of hemangiomas and suggested that growth factors may play a role in the pathogenesis of hemangiomas (Boye et al. 2001; Yu et al., 2001). Our laboratory has previously shown that autocrine production of vascular endothelial growth factor (VEGF) by endothelial cells results in malignant transformation to angiosarcoma (Arbiser et al., 2000; McLaughlin et al., 2000). Therefore, we postulated that another factor, which acts as an endothelial chemoattractant and survival factor, is responsible for autocrine growth in hemangiomas. Here, we demonstrate that the tie-2 receptor is constitutively phosphorylated in human hemangioma, implicating either constitutive activation of tie-2 or deregulated production of angiopoietin-2 (ang-2) as a causative factor in hemangiomagenesis. To elucidate the functional role of these agents in the pathogenesis of hemangioma, we used a murine model of hemangioma, bEnd.3 cells (Bautch et al., 1987; Williams et al., 1989), and found that these cells express both tie-2 and its ligand, ang-2. We also demonstrate that functional blockade of tie-2 using a soluble receptor inhibits the growth of bEnd.3 hemangiomas in vivo. Surprisingly, tie-2-deficient endothelial cells were also capable of initiating hemangiomas in vivo, implicating aberrant ang-2 production as a potential cause of hemangiomas. Nicotinamide adenine dinucleotide phosphate (reduced form) oxidase (Nox) genes have previously been linked to the angiogenic switch, and have been known to regulate ang-2 (Arbiser et al., 2002; Krikun et al., 2002). As we were unable to inhibit ang-2 stably using small interfering RNA, we discovered novel inhibitors of ang-2 production through blockade of Nox genes. These inhibitors nearly abolish bEnd.3 hemangioma growth in vivo. Thus, our data suggest that neutralization of ang-2 through Nox inhibition may be an effective therapy for hemangiomas of infancy.

Results

Tie-2 and ang-2 are Highly Expressed in bEnd.3 Hemangiomas In Vivo

In order to determine whether bEnd.3 hemangiomas exhibit potential autocrine loops involving tie-2 and angs, we performed in situ hybridization of lesions in mice. We found that bEnd.3 hemangiomas exhibit expression of both ang-2 and tie-2. Vascular endothelial growth factor receptor I and 2 were expressed at high levels, consistent with active endothelial remodeling, and small quantities of VEGF mRNA were observed. Use of control sense probes for VEGF did not reveal hybridization. No significant hybridization for ang-1 was observed (data not shown).

Inhibition of ang-2 Using a Soluble Receptor Inhibits bEnd.3 Growth In Vivo

Figure 1B:
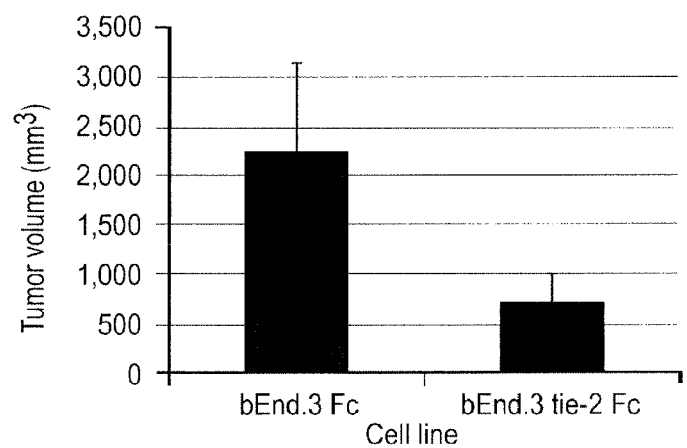

To determine whether inhibition of ang-2 expression by blockade of its receptor, tie-2, was needed for hemangioma formation in vivo, bEnd.3 cells were infected with adenoviruses encoding either soluble tie-2/Fc or adenoviruses encoding Fc fragment alone, 24 hours before injection. This treatment resulted in an approximately 66% decrease in tumor volume, compared to control adenovirus treatment (FIG. 1). No toxicity was observed as a consequence of infection in any of the three animals that were used in each group. Attempts to generate stably infected bEnd.3 cells with lentiviral small interfering RNA for ang-2 were unsuccessful, possibly owing to a requirement for ang-2/tie-2 signaling for longer term growth.

Tie-2 is not Required for In Vivo Growth of Hemangiomas

Given that functional blockade of the tie-2 receptor significantly reduced hemangioma formation in vivo, we wanted to determine whether this was the result of impaired ang-2 signaling or tie-2 inhibition. Polyoma-expressing endothelial cells derived from tie-2-deficient mice were injected into nude mice, and compared to controls, no significant difference in tumor volume or histology was noted. Efforts to generate bEnd.3 clones expressing small interfering RNA to ang-2 were unsuccessful, perhaps owing to severe growth disadvantages.

Triarylmethane Dyes Inhibit Nox Activity

Triarylmethane dyes were examined for activity against nox enzymes because they have chemical similarity to diphenyliodonium (DPI), a specific Nox inhibitor. Additionally, brilliant green and gentian violet have a long history of animal and human exposure, and gentian violet is Food and Drug Administration approved for human use. Brilliant green and gentian violet inhibited Nox2 and Nox4, the species of nox enzymes that are known to be expressed in endothelial cells, in a dose-dependent manner (FIGS. 2a and b).

Figure 2A:
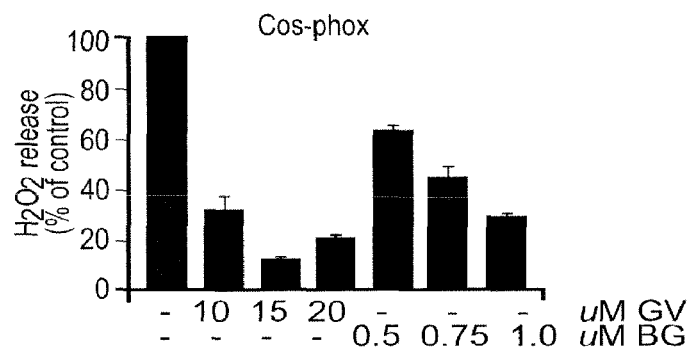
FIGS. 2a and 2b are charts showing that brilliant green (BG, 4-[(4-dimethylaminophenyl)-phenyl-methyl]-N,N-dimethyl-aniline) and gentian violet (GV, hexamethyl pararosaniline chloride) inhibit (a) Nox2 (Cos-phox),) and (b) Nox4 activity, along with hydrogen peroxide ($H_2O_2$) production in a dose-dependent manner in Cos-phox and HEK293 Nox4-11 cells.
Figure 2B:
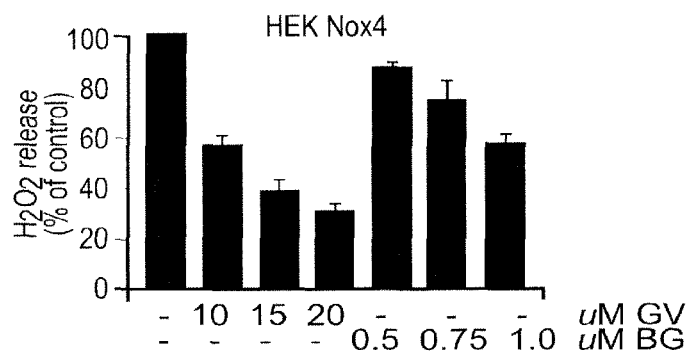

As shown in FIGS. 2a and 2b, cells were treated with different concentrations of vehicle control, BG, or GV; Cos-phox cells were additionally either left unstimulated or stimulated with phorbol 12-myristate 13-acetate. After 1 hour incubation at 37° C., the reaction was stopped and $H_2O_2$ production was measured using the homovanillic acid assay. The ability of these drugs to inhibit production of $H_2O_2$ is shown as a percentage relative to the untreated control (100%). Cox-phox cells did not produce $H_2O_2$ without phorbol 12-myristate 13-acetate stimulation with or without the addition of BG or GV (not shown). Optimal Nox2 activity requires phorbol 12-myristate 13-acetate stimulation whereas Nox4 activity is constitutive.

DPI and Triphenylmethane Dyes Such as Brilliant Green and Gentian Violet Inhibit ang-2 In Vitro Because DPI, brilliant green, and gentian violet all inhibit Nox genes, we wanted to see if they had similar effects on ang-2 mRNA expression. bEnd.3 cells were treated for 6.5 hours with either DPI or varying concentrations of brilliant green or gentian violet, and quantitative reverse transcription-PCR revealed a statistically significant decrease in ang-2 expression in all three treatment groups.

Treatment with 10 μM DPI resulted in an 80% decrease in ang-2 expression, compared to control (data not shown), whereas treatment with brilliant green had a marked dose-dependent effect on ang-2 production, such that 0.75 μM concentrations were sufficient to render ang-2 mRNA undetectable (FIG. 2a). Gentian violet increased ang2 expression at both the 1 and 5 μM concentrations, compared to control, but higher concentrations effectively inhibited ang-2 mRNA by 70-90% (FIG. 2b).

Treatment of bEnd.3 cells with (a) brilliant green and (b) gentian violet decreases levels of ang-2 mRNA (corrected for 18S RNA). Bars shown represent the average of triplicate experiments, and error bars indicate the standard error of the mean.

Brilliant Green and Gentian Violet Inhibit Hemangioma Formation In Vivo

Figure 3A:
FIGS. 3a and 3b are a photograph and a chart showing the effect of brilliant green and gentian violet on bEnd.3 hemangiomas in vivo. Photos (FIG. 3a) above represent average tumor burden in each of the three groups and tumor volume ($mm^3$) is graphically depicted.
Figure 3B:
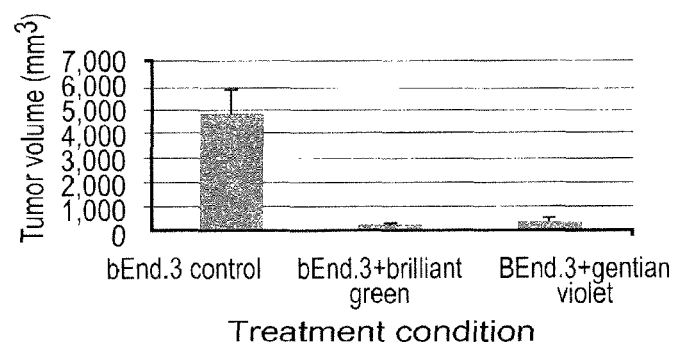
Figure 4:
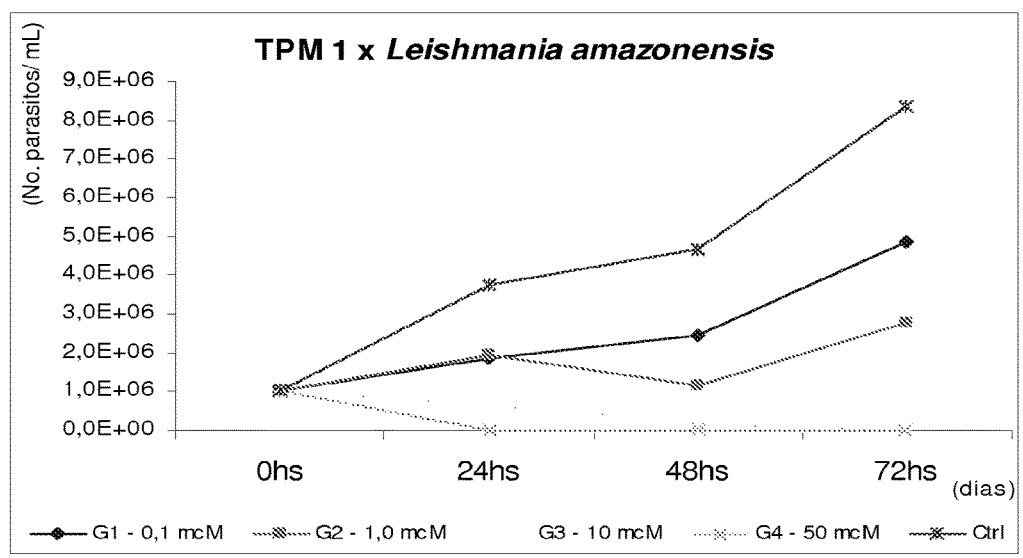
FIGS. 4-7 are graphs showing the effectiveness of triphenylmethane compounds TPM1, TPM2, TPM3, and TPM5, respectively, at treating Leishmania amazonensis, as measured by the number of parasites/mL over time (hours). The graphs show results at 0.1, 1.0, 10, and 50 mcM concentrations.
Figure 5:
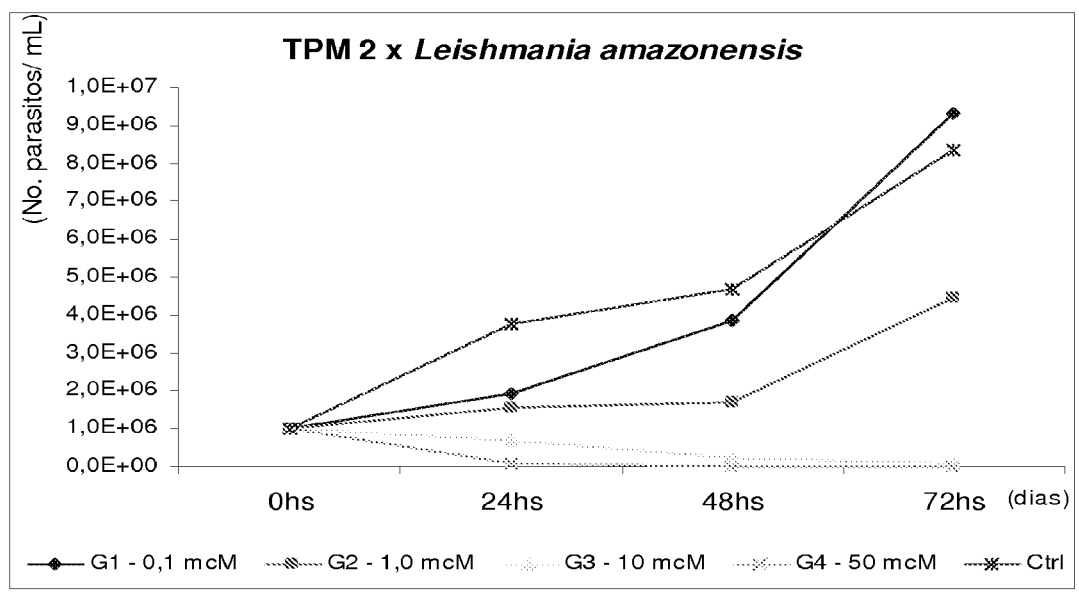
Figure 6:
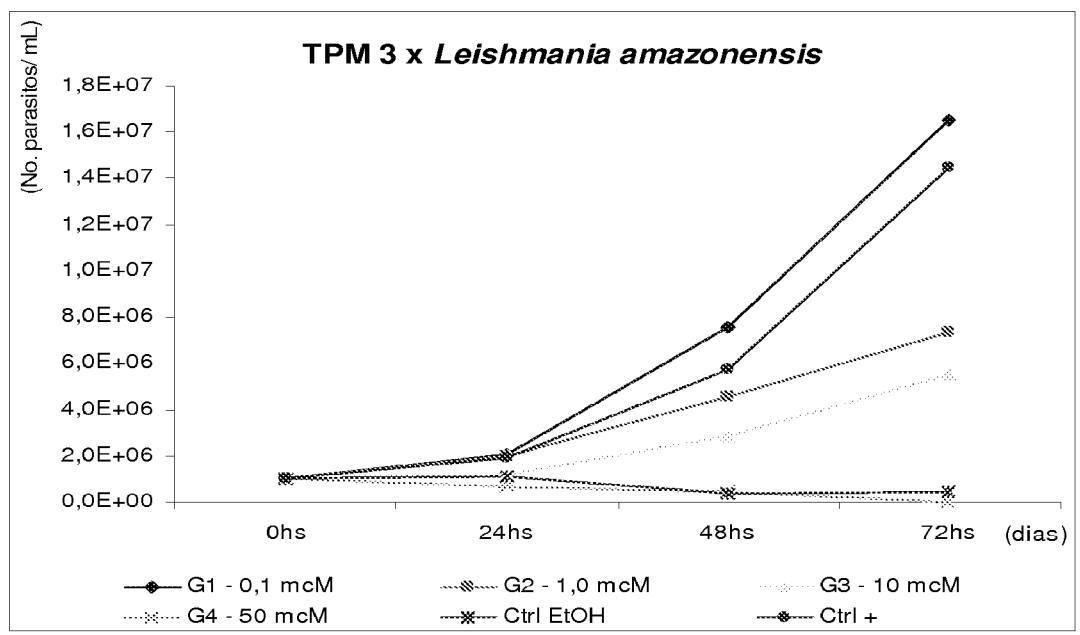
Figure 7:
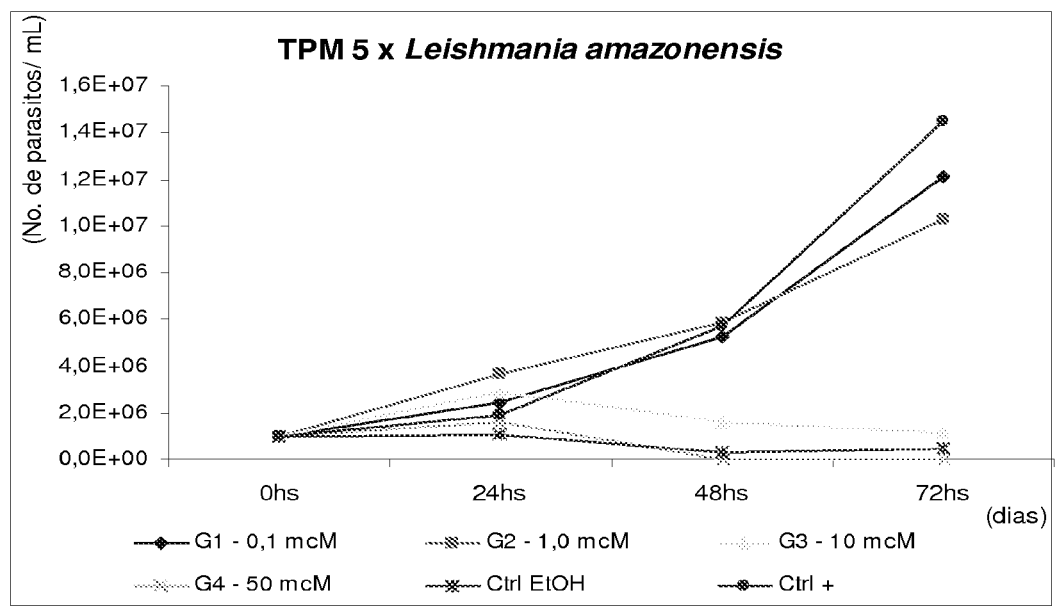

In order to determine if compounds that inhibit ang-2 formation in vitro would ameliorate hemangioma formation in vivo, we injected one million bEnd.3 cells subcutaneously into nine nude mice. Intralesional treatment of hemangiomas with either vehicle control, brilliant green, or gentian violet resulted in a 95.7 and 92.6% decrease in tumor size and arrest of tumor progression in both the brilliant green and gentian violet treatment groups, respectively, compared to control (FIGS. 3a and 3b). Neither local nor systemic toxicity was observed in any of the nude mice as a result of treatment.

For each treatment condition, three mice were injected with 1,000,000 bEnd.3 cells and received intralesional injection with either vehicle control, brilliant green or gentian violet (from left to right in photo) on days 9 and 14. Animals were euthanized on day 20, secondary to tumor burden in the control animals. The results are shown in FIGS. 3a and 3b.

Discussion

Hemangiomas are the most common cutaneous vascular lesions of childhood and are present in 5% of infants at 1 year of age. They may grow to large sizes and may result in compression of vital structures or high-output cardiac failure. Treatment of large hemangiomas may require lengthy courses of steroids or alpha IFN, which induces endothelial apoptosis, or surgery. These treatments are associated with a high level of morbidity, including growth retardation, infection, and irreversible neuropathy (Barlow et al., 1998). A significant number of these hemangiomas do not respond to treatment, resulting in death (Paller et al., 1983; Mulliken et al., 1982; Blei et al., 1998; Enjolras, 1998; Williams III et al., 2000). Thus, novel therapies are needed for hemangiomas in humans.

The growth factors required for hemangioma formation have not been fully elucidated. We have previously shown that angiosarcomas express VEGF, and overexpression of VEGF leads to the development of angiosarcoma (Arbiser et al., 2000). Hemangiomas express VEGF protein but little VEGF RNA, and it is highly likely that the VEGF protein may arise in surrounding cells, such as overlying skin (Cerimele et al., 2003). Similarly, we have recently demonstrated that verruga peruana, a hemangioma-like condition caused by endothelial infection with the bacterium *Bartonella bacilliformis*, exhibits high-level expression of ang-2 in vivo, and that infection results in the induction of ang-2 in vitro, whereas VEGF expression is limited to the overlying epidermis (Cerimele et al., 2003). Tie-2 expression has also been demonstrated in oral hemangiomas, but its functional role is unknown (Sato, 2002).

We thus postulated that other receptor tyrosine kinases may be important in the pathogenesis of hemangioma of infancy. Hemangiomas differ biologically from angiosarcomas in that they regress rather than cause progressive growth and metastasis.

Murine models of hemangioma, including the bEnd.3 model we used, exist through infection of neonatal endothelial cells with polyoma virus or polyoma middle T antigen. These models differ from angiosarcoma in that they grow through recruitment of host endothelium rather than active mitosis and they do not metastasize as murine SVR cells do (Williams et al., 1989; Arbiser et al., 1997). In this study, we show that tie-2 is activated in vivo in human hemangioma tissue, suggesting a physiologic role. We also demonstrate for the first time that bEnd.3-derived hemangioma cells, like human hemangiomas, produce ang-2 and tie-2, with a small contribution of VEGF (FIGS. 2 and 3).

Both ang-1 and -2 are required for viability in mice, as knockouts cause lethal vascular abnormalities in urtero (Suri et al., 1996; Maisonpierre et al., 1997). Each binds and activates the tie-2 receptor, leading to downstream events such as activation of phosphoinositol-3 kinase (Suri et al., 1996), and both peptides have been shown to promote angiogenesis in the presence of VEGF. However, they have opposing effects in vivo. Transgenic overexpression of ang-1 leads to non-permeable vessels, but ang-2 expression leads to leaky vessels (Suri et al., 1998; Thurston et al., 1999). Mg-1 is preferentially expressed by stromal cells, whereas ang-2 is highly expressed by tumor cells (Tanaka et al, 1999) and, as we demonstrate in this study, hemangioma model cells. Overexpression of ang-1 in tumor cells leads to increased vessel maturation and decreased in vivo growth (Hawighorst et al., 2002; Stoeltzing et al., 2002). Thus, it is unlikely that ang-1 plays a predominant role in the pathogenesis of proliferative vascular lesions such as hemangioma.

Our results suggest novel therapies for hemangioma of infancy and demonstrate similarities between the polyoma-induced hemangiomas, which have been known to induce hemangiomas through the recruitment of host endothelial cells or endothelial precursor cells, and human hemangiomas (Whitman et al., 1985; Williams et al., 1989; Dahl et al., 1998). Soluble receptors antagonizing both ang-1 and -2 may have the benefit of inhibiting not only the remodeling effect of ang-2 but also the antiapoptotic effect of ang-1. Our study with tie2-deficient endothelium suggests that aberrant expression of ang-2, rather than constitutive activation of tie-2, is required for hemangiomagenesis. Constitutively active mutations in tie-2 have been found in vascular malformations, but not in hemangiomas, and these activating mutations in tie-2 are associated with phosphoinositol-3 kinase (Vikkula et al., 1996). Naturally occurring mutations of tie-2 have also been shown to be transforming when introduced into immortalized endothelial cells, likely through prevention of apoptosis. This differs from endothelial cells present in human hemangiomas, which undergo apoptosis with age. These findings support our hypothesis that aberrant production of ang-2, rather than constitutive tie-2 activation, is required for hemangioma growth in vivo. Interestingly, introduction of a vascular malformation-associated tie-2 allele into immortalized endothelial cells leads to malignant transformation (Wang et al., 2004). Our results differ in that in vivo growth of hemangiomas is dependent on ang-2, rather than tie-2, and may reflect basic biologic differences between hemangiomas and vascular malformations. Attempts to generate bEnd.3 clones expressing small interfering RNA to ang-2 were unsuccessful, perhaps reflecting a requirement of ang-2 for hemangioma growth.

We have previously shown that reactive oxygen induces angiogenesis and that blockade of Nox genes results in decreased angiogenesis (Arbiser et al., 2002). Based upon this observation, we examined the ability of DPI, a known Nox inhibitor, to donwregulate ang-2 expression. DPI is structurally similar to the triphenylmethane dye family, as it forms a cation directly attached to multiple aromatic rings. Triphenylmethane dyes such as gentian violet and brilliant green have a long history of human and veterinary use. We demonstrate that like DPI, gentian violet and brilliant green decrease expression of ang-2 in vitro and, consistent with this activity, decrease growth of bEnd.3 hemangiomas in vivo. Inhibitors of Nox genes may have therapeutic utility in the treatment of hemangiomas.

Materials and Methods

Cells bEnd.3 cells (ATCC CRL 2299) were obtained from the American Type Culture Collection (Manassas, Va.) and cultured in DMEM (4,500 mg glucose/l; Sigma-Aldrich, St Louis, Mo.) supplemented with 10% fetal bovine serum, L-glutamine (14 ml/l), recombinant mouse VEGF (10 ng/ml; R&D Systems, Minneapolis, Minn.), and antibiotic/antimycotic (14 ml/l; Sigma-Aldrich). HEK293-Nox4-11 cells and COS-phox cells have been described previously (Price, 2002; Martyn, 2006).

In Situ Hybridization

In situ hybridization was performed on 4 mm sections of formalin-fixed, paraffin-embedded tissue. Details of in situ hybridization have been reported previously (Arbiser et al., 2000; McLaughlin et al., 2000). Slides were passaged through xylene and graded alcohols; 0.2 M HCl; Tris/EDTA with 3 mg/ml proteinase K/0.2% glycine/4% paraformaldehyde in phosphate-buffered saline (pH 7.4); 0.1 M triethanolamine containing 1/200 (vol/vol) acetic anhydride; and 2× standard sodium citrate. Slides were hybridized overnight at 50° C. with $^{35}$S-labeled riboprobes in the following mixture: 0.3 M NaCl/0.01 µM Tris (pH 7.6)/5 mM EDTA/0.02% (wt/vol) Ficoll/0.02% (wt/vol) polyvinylpyrollidone/0.02% (wt/vol) BSA fraction V/50% formamide, 10% dextran sulfate/0.1 mg/ml yeast tRNA/0.01 µM dithiothreitol. Post-hybridization washes included 2× standard sodium citrate/50% formamide/10 mM dithiothreitol at 50° C., 4× standard sodium citrate/10 mM Tris, I mM EDTA with 20 mg/ml ribonuclease at 37° C.; and 2× standard sodium citrate/50% formamide/10 mM EDTA at 65° C. and 2× standard sodium citrate. Slides were dehydrated through graded alcohols containing 0.3 M ammonium acetate, dried, coated with Kodak NTB 2 emulsion (Rochester, N.Y.), and stored in the dark at 4° C. for 2 weeks. The emulsion was developed with Kodak D 19 Developer, and the slides were counterstained with hematoxylin. $^{35}$S-labeled single-stranded antisense and sense RNA probes for mouse VPF/VEGF, ang-1, -2, and tie-2 mRNA and the mouse VPF/VEGF receptors, vascular endothelial growth factor receptor 1 and 2 mRNAs, were described previously (Arbiser et al., 2000; McLaughlin et al., 2000).

Adenoviral Infection and In Vivo Tumorigenesis Studies

The tie-2 Fc fusion construct was placed into an adenoviral cassette, and virus was prepared as described previously (Thurston et al., 2000). bEnd.3 cells were infected with tie-2 Fc or Fc control adenovirus at a multiplicity of infection of 5. Twenty-four hours after infection, one million cells were injected subcutaneously into three nude mice per treatment group. Mice were monitored for the development of tumors and killed I month after injection. No evidence of toxicity was observed as a result of infection. For experiments utilizing tie-2 knockout bEnd.3 cells versus wild-type bEnd.3 cells, one million cells were injected subcutaneously as above.

Determination of ROS Production $H_2O_2$ release was measured using the homovanillic acid assay as described previously (Martyn, 2006). Briefly, 1.5-1.75×10$^5$ cells/well of a 12-well plate were seeded. The following day, cells were washed once with Hank's balanced salt solution and then preincubated for 15 minutes with either gentian violet (10-20 μM) or brilliant green (0.5-1.0 μM) in 1 ml of media. The cells were then washed once with Hank's balanced salt solution. Gentian violet or brilliant green was added at the same concentrations as in pretreatment to 0.5 ml of homovanillic acid assay solution (100 μM homovanillic acid assay, 4 U/ml horseradish peroxidase in Hank's balanced salt solution with $Ca^{2+}$ and $Mg^{2+}$) and incubated with the cells for 1 hour at 37° C. Cos-phox cells were additionally stimulated with 0.4 μg/ml phorbol 12-myristate 13-acetate. The reaction was stopped by adding 75 μl of homovanillic acid assay stop buffer (0.1 M glycine/0.1 M NaOH (pH 12) and 25 mM EDTA in phosphate-buffered saline). Fluorescence was read on a BioTek Synergy HT (BioTek Instruments Inc., Winooski, Vt., CA) with an excitation of 320 nm and emission of 440 nm.

Quantitative Reverse Transcription-PCR for Ana-2 in bEnd.3 Cells Treated with Vehicle Control, Brilliant Green, or Gentian Violet bEnd.3 cells were seeded equally into six T-75 flasks and 24 hours later were treated with 0, 1, 5, 10, 15, and 20 μM concentrations of gentian violet (Sigma-Aldrich, no. G2039) in ethanol for 6.5 hours. RNA was extracted and purified using TRI reagent (Sigma-Aldrich, T9424) and measured using spectrophotometer (Perkin-Elmer UV/VIS, Wellesley, Mass.). RNA (1 μg) was used for DNase Amplification (Invitrogen, no. 18068-015, Carlsbad, Calif.) followed by first-strand synthesis for reverse transcription-PCR (Invitrogen SuperScript, no. 12371-019). 96-well Optical Reaction Plate (ABI PRISM, no. 128, Applied Biosystems, Foster City, Calif.) was used for the reverse transcription-PCR reaction. A measure of 2.5 μl of template, which had been diluted 1:10 in crosslinked water, was used in each well and the experiment was performed in triplicate. Ang pt2 (Applied Biosystems, Taqman Gene Expression Assay, Mm00545822_ml) and 18S (Applied Biosystems Taqman Gene Expression Assay, Hs999999901_sl) primers were used along with crosslinked molecular grade water (Cellgro, Mediatech. Inc., Herndon, Va.) and master mix (Applied Biosystems TaqMan Fast Universal PCR Master Mix (2×)). The reaction was run on the 7900 Applied Biosystems Reader for Absolute Quantification for 96-well plates. C values were analyzed by $\Delta\Delta C_t$ method, and the standard error of the mean was calculated (FIG. 3b). The same protocol was used for treatment with brilliant green (Sigma, no. B6756), except that the concentrations used were 0, 0.1, 0.25, 0.5, and 0.75 μM (FIG. 3a).

Treatment with Vehicle Control, Brilliant Green, or Gentian Violet In Vivo

For each treatment condition, three mice were subcutaneously injected with one million bEnd.3 cells and monitored for tumor development. On day 9, tumors were measured in all nine animals, and there was no significant difference in tumor volume before the initiation of treatment. Each mouse then received intralesional injection with either 0.33 ml vehicle control, brilliant green (5 mg/kg, dissolved in 100 ml ethanol and 900 μl intralipid) or gentian violet (5 mg/kg, dissolved in 100 μl ethanol and 900 μl intralipid) on days 9 and 14. No toxicity was noted following injection. Animals were euthanized on day 20, secondary to tumor burden in the control animals. Photos represent average tumor burden in each of the three groups (FIG. 3a), and tumor volume (mm$^3$) is graphically depicted (FIG. 3b). Error bars represent the standard error of the mean.

Example 4: Analysis of Triarylmethanes in Treating Parasitemia

A series of in vivo experiments were performed to evaluate the ability of the triarylmethanes, in particular, imipramine blue, to treat parasites, such as trypanosomes. The bloodstream forms of many, but not all, trypanosomes (a type of parasite) solely depend on trypanosome alternative oxidase (TAO), for respiration. Accordingly, those of the compounds described herein which can inhibit the TAO can effectively kill the parasite.

Gentian violet has been used as a trypanocidal agent for Chagas disease. The data presented herein show that it is also possible to inhibit *T brucei* oxidases using Gentian violet, analogues thereof, and other compounds described herein.

In one study, the parasite was *T. brucei*. Mice were injected with parasites (5,000 parasites/mouse), and injected (s.c) with imipramine blue (1 mg/mice/day) starting from the day the mice were injected with parasites. The parasitemia level in blood was counted on each following day.

The results showed that both the control and the imipramine-treated mice died at day 4 because of the parasite load. However, the number of the parasite/ml of blood were slightly less in the imipramine-treated mice.

The experiment was repeated with IV administration of imipramine blue (100 μg of imipramine blue). Because the parasite (*T. brucei*) grows in the blood and tissue fluid and does not enter into any cells, it was believed that IV administration could effectively target the parasites. This treatment resulted in a 70% decrease in parasitemia in the mouse model. However, a dosage of 1 mg IV killed the mice. Accordingly, it is important to find a therapeutic window (where treatment of parasitemia can be effected, without unwanted toxic effects). This therapeutic window is in the range of between about 150 and 250 μg.

Imipramine blue and ethylcarbazole blue also showed favorable cell toxicity to trypanosome toxicity at 500 nm. These and other compounds were tested on live cells.

The experiment was conducted with one million cells of the bloodstream form of *T. brucei*. After over night treatment with different compounds (at concentrations of 50 and 100 μmolar), cells were counted and plotted with controls. All cells died in gentian violet and brilliant green.

The results are as follows:

The $IC_{50}$ values for Gentian Violet (GB)<20 nM; Brilliant Green (BG) and Carbazole Blue (CB)<50 nM; Ethyl carbazole Blue (ECB) and Imipramine (IP) 50<100 nM.

Example 5: Treatment of *Malaria* Using Triarylmethanes

Imipramine blue, a triarylmethane analogue of imipramine, is a chemosensitizer, and useful in the treatment of *malaria*. Imipramine blue, as well as other triarylmethanes described herein, also has NADPH oxidase inhibitor activity, and some of these compounds have shown activity against trypanosomes and leishmania. While not wishing to be bound to a particular theory, it is believed that these compounds have dual activity against *malaria* through chemosensitization and inhibition of *Plasmodium* NADPH oxidase.

The compounds were tested in a *malaria* model using both chloroquine sensitive and multidrug resistant *P. falciparum*. The *malaria* model was the same as published in JAC Advance Access published online on Jul. 30, 2008, Journal of Antimicrobial Chemotherapy, doi:10.1093/jac/dkn315, the contents of which are hereby incorporated by reference, and the data is summarized in the table below.

Briefly, the assay involves exposing both chloroquine sensitive and multidrug resistant *P. falciparum* to the compounds. After one hour of exposure to the highest concentration of the compound, followed by removal of the compound, the growth of all stages of *P. falciparum* was observed. The reduction in the growth stages was then compared with untreated control parasites. Any stage-specific effects were noted at any of the concentrations. The presence of strong inhibition (defined herein as 10% growth) of all parasite stages was evaluated when the parasites were exposed to various concentrations of various compounds.

| Compound | $IC_{50}$ (nM) vs *P. falciparum* | |
|---|---|---|
| | D6 (Chloroquine Sensitive) | Dd2 (Multidrug Resistant) |
| Chloroquine Control | 7.9 | 139.6 |
| Gentian Violet (GV) | 12.1 | 0.44* |
| Brilliant Green (BG) | 71.2 | 126.8 |
| Methyl Brilliant Green (MBG) | 61.7 | 48.9 |
| Carbazole Blue (CB) | 66.2 | 51.0 |
| Imipramine Blue (IB) | ~2,500 | 825.8 |
| DDT Black | ~2,500 | 812.8 |
| Chrysin Black | 2,500 | 2,500 |

*may need retest

The data show that the active triphenylmethanes in this assay are carbazole blue and methylbrilliant green. The inactive ones are DDT black and chrysin black.

Example 6: Treatment of Leishmanlasis

In addition to the other parasitic diseases discussed in other examples, the compounds were also tested in a leishmaniasis model.

TPM1 (ethylcarbazole blue) has the best activity on *Leishmania* of the compounds tested so far. Preliminary data showed activity against in vitro promastigotes.

The experiments were started using water as a solvent for the triarylmethanes (TPM, standing for triphenylmethane). However, water was not an effective solvent, so ethanol was substituted. Ethanol is toxic to *leishmania*, so a control group was tested with a higher ethanol concentration than that present on the TPM groups. The results of the experiment are presented in FIGS. 4-8.

Each of FIGS. 4-7 has five or six groups with 50, 10, 1 and 0.1 mcM (micromolar) of TPMs (1, 2, 3 and 5) in ethanol, and two control groups: Ethanol 5% (50mcM) and positive control.

Figure 8:
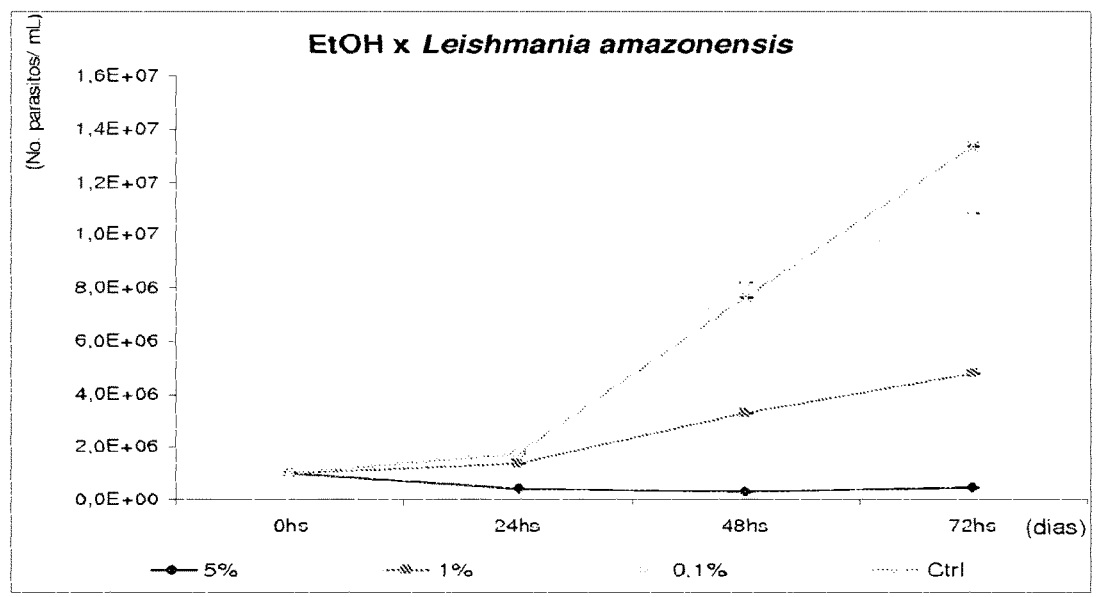
FIG. 8 is a graph showing the effectiveness of ethanol at treating Leishmania amazonensis, as measured by the number of parasites/mL over time (hours).

All of the compounds tested were found to have activity, but ethanol also was active. Accordingly, a separate experiment was conducted to determine how toxic the ethanol is without added compounds. Concentrations of 5, 1 and 0.1% of ethanol were used. FIG. 8 shows the effect of ethanol alone.

At the lower concentration (0.1% ethanol), no toxicity was observed at the first 48 hours. Thus, the results obtained in the first experiment with the last two concentrations of TPM in ethanol (1 and 0.1 mcM), where the concentration of ethanol were 0.1 and 0.01%, can be accepted (the dark blue and pink lines on the first four graphics). Thus, TPM1 and TPM 2 have shown activity in these concentrations, while TPM 3 and TPM 5 did not.

Figure 9:
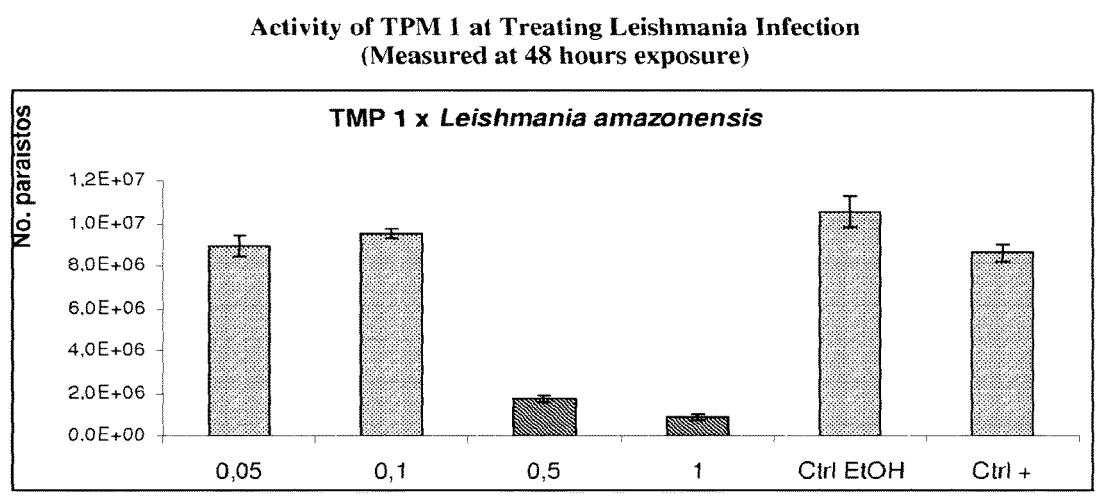
FIGS. 9-14 are graphs showing the effectiveness of compounds TPM1, TPM2, TPM6, TPM7, TPM9, and TPM10, respectively, at treating Leishmania amazonensis, as measured by the number of parasites/mL over time (data taken 48 hours after exposure to the compounds). The graphs show results at 0.05, 0.1, 1, and 5 mcM concentrations, with ethanol as a control.
Figure 10:
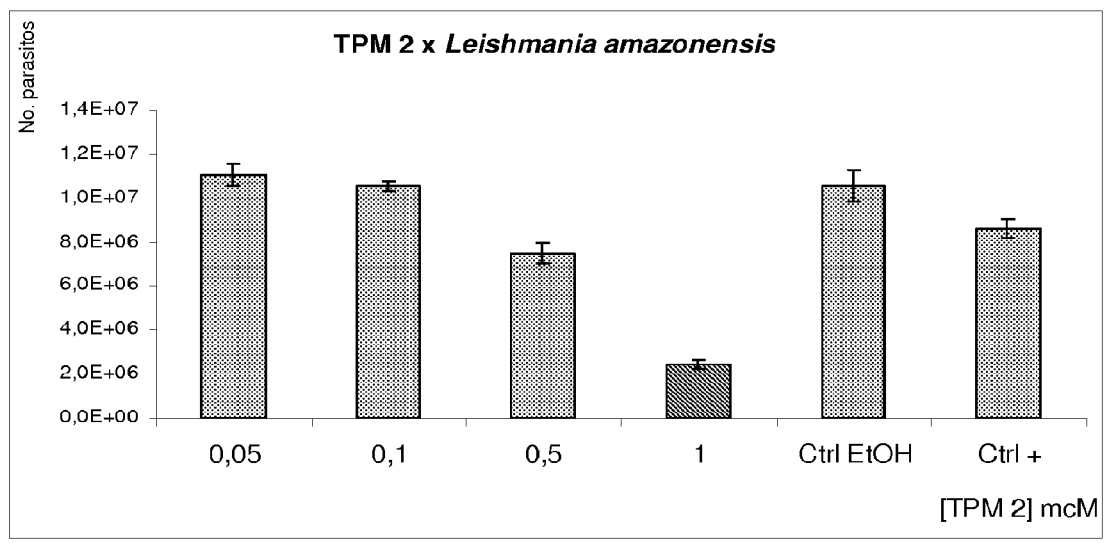
Figure 11:
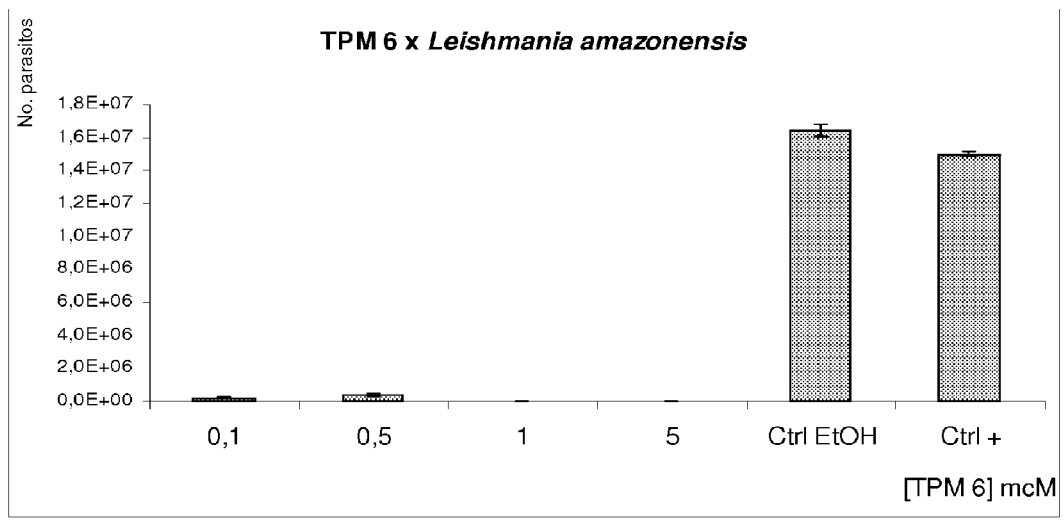
Figure 12:
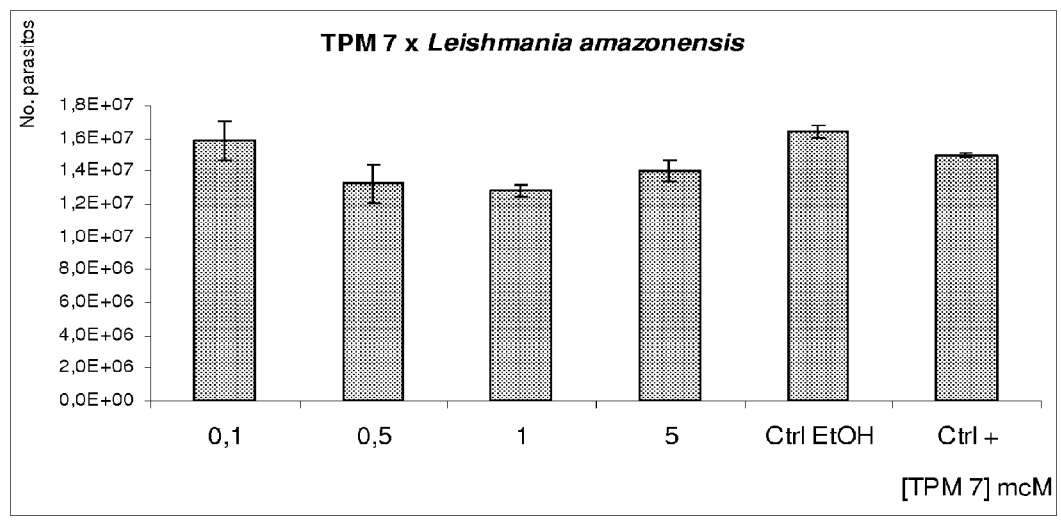
Figure 13:
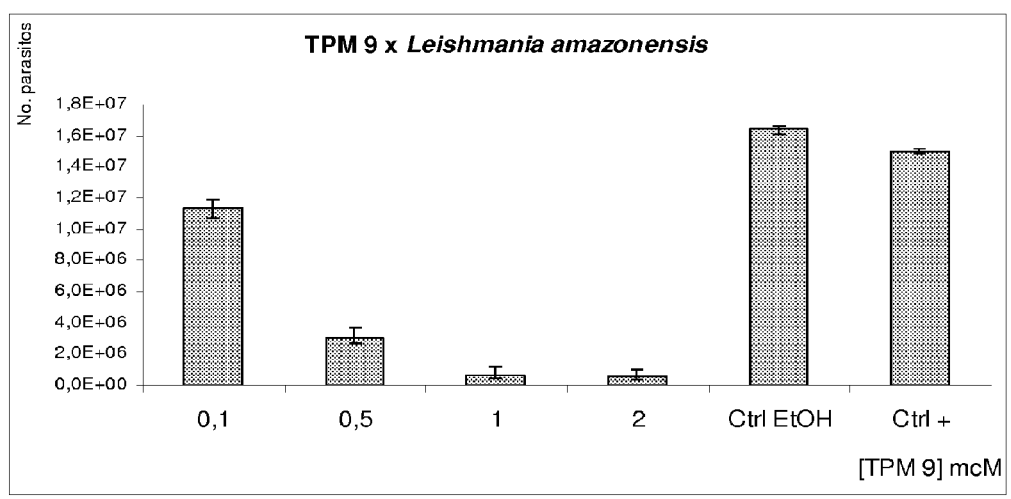
Figure 14:
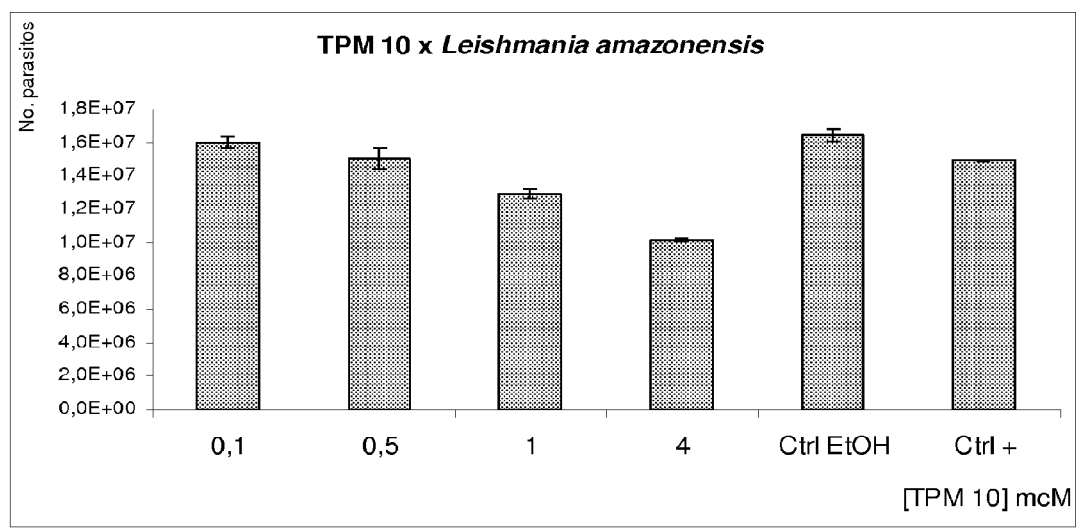
Figure 15:
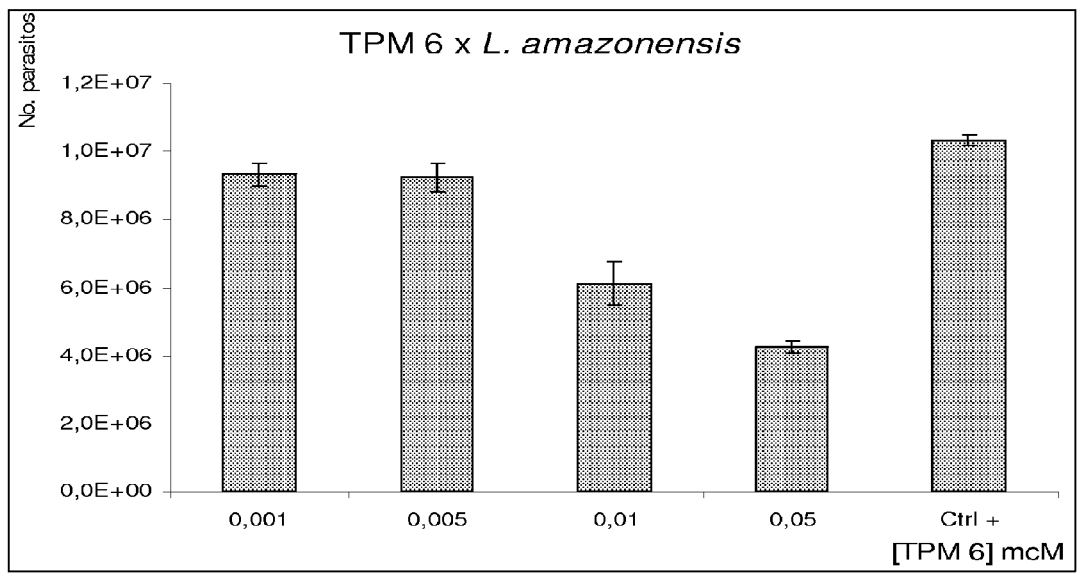
FIG. 15 is a graph showing the effectiveness of compound TMP6 at treating Leishmania amazonensis, as measured by the number of parasites/mL over time (data shown was measured 48 hours after exposing the parasite to the compound). The graphs show results at 0.001, 0.005, 0.01, and 0.05 mcM concentrations, with ethanol as a control.

To confirm these data, another experiment was performed with TPM 1 (ethylcarbazole blue) and TPM 2 with 1; 0.5; 0.1 and 0.05 mcM, where the ethanol was present in a non-toxic concentration. The number of parasites was counted only after 48 hours. Again, an ethanol control at 0.1% was used. The results are shown in FIGS. 9-10.

With this new experiment, it was found that TPM 1 (ethylcarbazole blue) has significant activity at 0.5 and 1mcM, where the growth inhibition was 80 and 90%, respectively and TPM 2 at 1 mcM, where the growth inhibition was 72%. The $IC_{50}$ was around 0.3 mcM for TPM1 and 0.6 mcM for TPM 2.

The $IC_{50}$ was calculated by the method described by Hills et al. (18) and Huber and Koella (19). Briefly, Hills proposed finding two concentrations, $X_1$ and $X_2$, such that the parasite density, Y1, at concentration $X_1$ (and all lower concentrations) was more than half of the density found in the control, $Y_0$, and that the parasite density. $Y_2$, at concentration $X_2$ (and all higher concentrations) was less than half of $Y_0$. The $IC_{50}$ was then found by linear extrapolation between $X_1$ and $X_2$:

$$\log(IC_{50}) = \log(X_1) + [(Y_1 - Y_0/2)/(Y_1 - Y_2)][\log(X_2) - \log(X_1)].$$

Compounds TPM 6 (MW=400.60), TPM 7 (MW=672.86), TPM 9 (MW=521.76) and TPM 10 (MW=662.95) were evaluated with the same methodology. They were tested using a maximum of 1% of ethanol in each treatment group. The ethanol control was also evaluated with the same concentration (1%).

The treatment groups were as follows:
TPM 6 and TPM 7: 5; 1; 0.5 and 0.1 mcM.
TPM 9: 2; 1; 0.5 and 0.1 mcM.
TPM 10: 4; 1; 0.5 and 0.1 mcM.

The highest concentration of each compound was different in each group because the compounds were solubilized in 25 mL of ethanol, and each compound has a different molecular weight and solubility in ethanol. The compounds had to be soluble in the maximum of ethanol allowed (i.e., 25 mL).

TPM 6 and 9 showed promising results. The data is shown in FIGS. 11-15. As shown in the figures, the most active compound is TPM6 (methyl brilliant green), while the next most active compounds are TPM1 (ethylcarbazole blue) and TPM9 (proton sponge).

Preliminary data showed activity against in vitro promastigotes (the flagellate stage of a trypanosomatid protozoan).

The data show that:
- TPM 6 (methylbrilliant green) has significant activity at 0.1; 0.5; 1 and 5 mcM with p<0.001%, where the growth inhibition was 98, 98, 100 and 100% respectively.
- TPM 7 has significant activity at 1 mcM with p<0.05%, where the growth inhibition was 14.5%.
- TPM 9 has significant activity at 0.1; 0.5; 1 and 2 mcM with p<0.001%, where the growth inhibition was 24.5; 80, 96 and 96.5% respectively. The $IC_{50}$ was around 0.2mcM.
- TPM 10 has significant activity at 1 and 4 mcM with p<0.01 and 0.001% respectively, where the growth inhibition was 13.5 and 32%.

The $IC_{50}$ could not be calculated, with this method, for compounds that did not have values under and up to 50% of growth inhibition, like TPM 6, TPM 7 and TPM 10.

The results of all of these experiments are summarized in the following table.

| Experiment | TPM | MW | $IC_{50}$ |
|---|---|---|---|
| 1 and 2 | TPM 1 | 502.71 | 0.3 μM |
| 1 and 2 | TPM 2 | 588.87 | 0.6 μM |
| 1 | TPM 3 | 455.46 | 1.0 μM |
| 1 | TPM 5 | 512.69 | 1.0 μM |
| 3 and 4 | TPM 6 | 400.60 | 0.02 μM |
| 3 | TPM 7 | 672.86 | 5.0 μM |
| 3 | TPM 9 | 521.76 | 0.2 μM |
| 3 | TPM 10 | 662.95 | 4.0 μM |

To calculate the $IC_{50}$ of TPM 6 (MW=400.60), it was tested again following the same methodology.

The treatment groups were TPM 6 at a dosage of 0.05; 0.01; 0.005 and 0.001 mcM. The data showed that:
- TPM 6 has significant activity at 0.01 and 0.05 mcM with p<0.001%, where the growth inhibition was 41 and 59% respectively. The $IC_{50}$ was around 0.02mcM.

Example 7: Use of Imipramine Blue to Induce Apoptosis and Cell Cycle Arrest in Myeloma Cells—Mediated in a p53 Dependent Pathway Background:

Tricyclic antidepressant drugs imipramine, clomipramine and citalopram induce neurogenesis (1) and are also known to induce apoptosis in cancer cells (2). However, the molecular mechanism underlying the therapeutic effects of these drugs in various intracellular signaling pathways and possibly a clinical utility of one these compounds in cancer treatment has not been well explored. Imipramine blue has been recently shown to inhibit CDK inhibitor p21 expression and subsequent release of neuronal progenitor cells from the blockade of proliferation (3). Imipramine blue treatment induces extensive DNA damage in cultured C6 rat glioma cells (4) and induces cell growth inhibition (5).

Aim:

The aim of this investigation was to determine the capacity of imipramine blue in cell growth inhibition and its potency to induce apoptosis in myeloma cells as well as in various hematological cancer cell types.

Materials and Methods:

Imipramine blue was obtained from the department of dermatology. Emory University. MTT assays for myeloma cells (MM.1S, MM.1R, RPM18226, and U266) were used to evaluate the cell viability. AnnexinV staining and cell cycle analysis was done by flow cytometry to assess the level of apoptosis and analyze cell cycle arrest. Western blotting was performed using antibodies to analyze the impact of imipramine blue on various targets. Bone marrow from myeloma patients were obtained with consent from the Winship Cancer Institute.

Results:

When myeloma cells were treated up to 72 hrs, the cell viability assays showed that treatment of imipramine blue up to 10 μM results in more than 80% growth inhibition effectively between 6 uM to 10 μM. Apoptosis assay by annexin V staining shows that the cells were induced to undergo apoptosis with similar concentrations. Procaspases (caspase 8, 9, 3 and PARP) were extensively cleaved from a low concentration as low as 0.5 μM to 10 μM imipramine blue in about 48 hrs. DNA damage was observed based on the elevated levels of phos-p53 and GADD45 in MM.1S cells. The cell cycle profile indicated that imipramine blue induces both cell cycle arrests as well as apoptosis in MM.1S cells. Combining imipramine blue either with bortezomib or perifosine suggested that there is additive benefit in combination. Imipramine blue overcomes the growth advantage by cytokines IL-6 and IGF1 in MM.1S cells. Imipramine blue induced cell growth inhibition in both leukemia and in lymphoma cell lines. Primary cells obtained from myeloma patients showed a very significant cell killing of CD38 positive population by imipramine blue, either alone as a single agent or in combination with bortezomib. The phos-AKT was not significantly reduced while both phos-p53 and GADD45 were upregulated as a result of imipramine blue treatment in MM.1S.

Conclusion:

Imipramine blue has a potential to induce apoptosis and cell cycle arrest in both myeloma as well as in primary myeloma cells, and also in other hematological cancer cell types. The cellular response seems to be mainly through DNA damage, apoptosis, and cell cycle arrest. Imipramine blue is believed to have clinical utility in the treatment of hematological cancer.

REFERENCES

1. The antidepressants imipramine, clomipramine, and citalopram induce apoptosis in human AML (HL-60) cells via caspase-3 action. Xia et. al. J. Biochem Mol. Toxicology. 1999; 13; 338-347
2. Effects of imipramine on ion channels and proliferation of IGR1 melonoma cells. Journal of Membr Biol. 2002; 188:137-149
3. p21 $^{Cip}$1 restricts neuronal proliferation in the subgranular zone of the dentate gyrus of the hippocampus. Pechnick, et al. 2008; PNAS; 105, 1358-1363
4. Assessment of DNA damage in C6 glioma cells after antidepressant treatment using alkaline comet assay. Slamon et. al. Arch. Toxicol. 2001; 75; 243-250

5. Chronic Treatment With Imipramine Inhibits Cell growth and Enhances Serotonin 2C Receptor mRNA Expression in NG 108-15 Cells. Sukma, et. al. J Pharmacol Sci. 2003:92.433-436

Example 8: ESR Spectrum of a Representative Triarylmethanes and Superoxide Dismutase Li used ESR to confirm the production of NADPH-dependent .O2- by isolated endosomes (Li et al., *Molecular and Cellular Biology*, January 2006, p. 140-154, 26(1):140-154 (2006)). ESR assays were conducted at room temperature using a Bruker model EMX ESR spectrometer (Bruker). Vesicular fractions from each sample were mixed with the spin trap, 50 mM 5,5-dimethyl-1-pyrroline N-oxide (DMPO), in a total volume of 500 µl of PBS, pH 7.4. This solution contained iminodiacetic acid-chelating resin (10 ml/liter; Sigma-Aldrich). The reaction was initiated by adding NADPH to 100 µM and was immediately placed into the ESR spectrometer. DMPO-hydroxyl radical adduct formation was assayed for 10 min. Instrument settings were as follows: receiver gain, $1\times10^6$; modulation frequency, 100 kHz; microwave power, 40.14 mW; modulation amplitude, 1.0 G; and sweep rate, 1 G/s.

Figure 16:
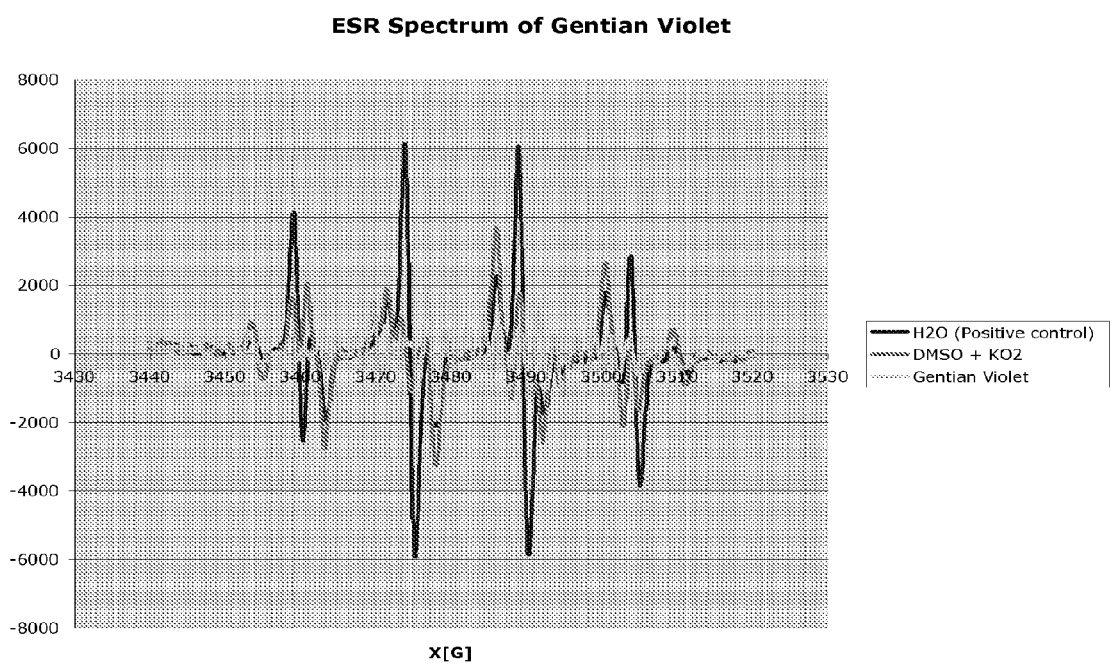
FIG. 16 is an ESR spectrum of gentian violet
Figure 17:
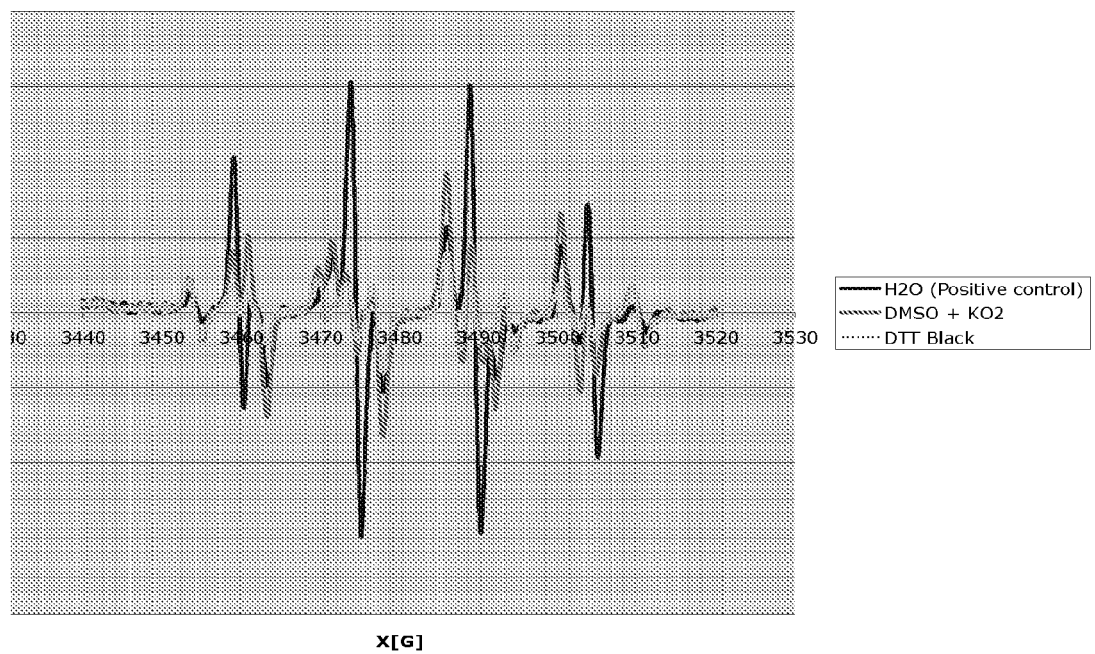
FIG. 17 is an ESR spectrum of DTT black.
Figure 18:
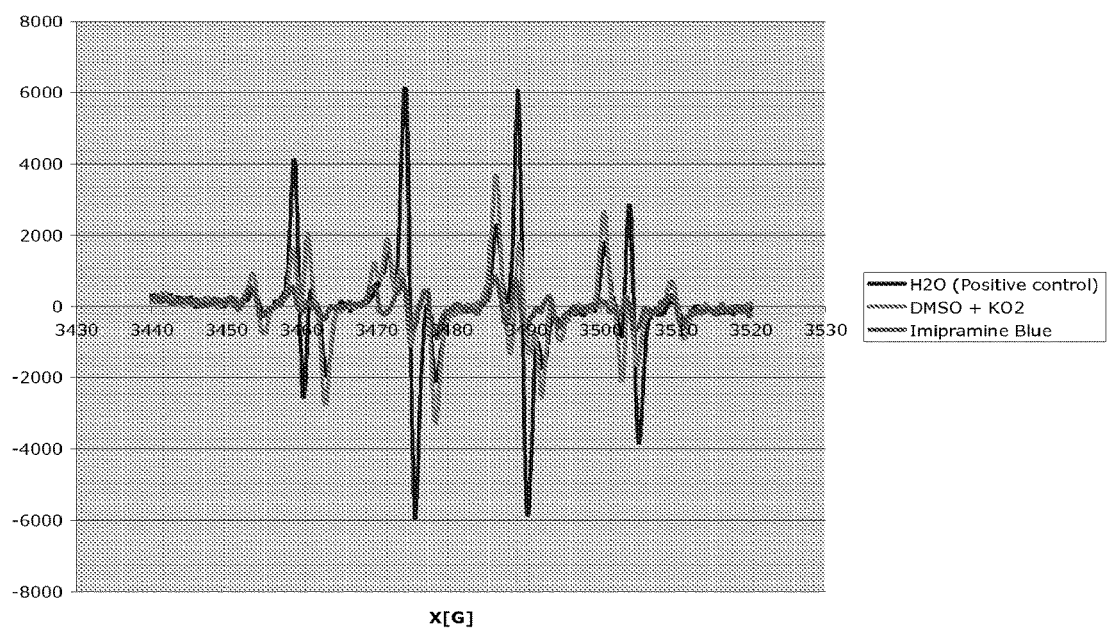
FIG. 18 is an ESR spectrum of imipramine blue.

In the instant application, the ESR spectrum of gentian violet, DTT black, and imipramine blue, and of superoxide dismutase were taken using conditions substantially as described in Li et al. The ESR spectra (FIGS. 16-18) show that these triarylmethane compounds appear to form a radical by reacting with superoxide, thus inhibiting the ability of superoxide dismutase to generate ROS.

The present invention is not to be limited in scope by the specific embodiments described herein. Indeed, various modifications of the invention in addition to those described will become apparent to those skilled in the art from the foregoing description and accompanying figures. Such modifications are intended to fall within the scope of the appended claims.

Various publications are cited herein, the disclosures of which are incorporated by reference in their entireties.

The invention claimed is:

1. A pharmaceutical composition comprising liposomes containing a compound defined by the formula below

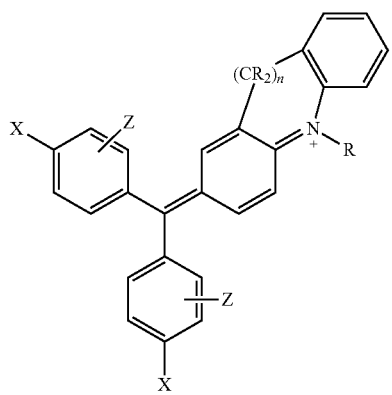

or a pharmaceutically acceptable salt thereof, wherein
n is 1-4;
R is H or substituted or unsubstituted alkyl, alkenyl, alkynyl, aryl, heteroaryl, alkylaryl, or arylalkyl;
X is H, amino, hydroxy, ether, thiol, or thiolether; and
Z is an optional substituent selected from halo, hydroxyl, thiol, ester, amide, carboxy, sulfoxy, nitrile, azido, alkyl, alkenyl, alkynyl, nitro, amino, aryl, heteroaryl, phosphonate, and fulvene.

2. The composition of claim 1, wherein the compound is defined by formula

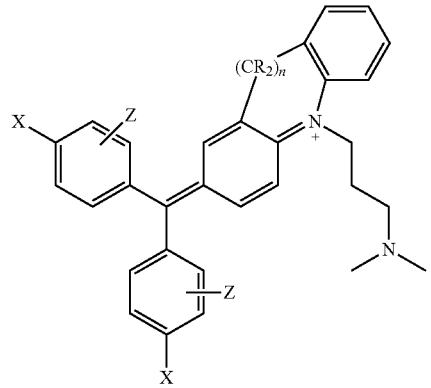

3. The composition of claim 1, wherein the compound is defined by formula

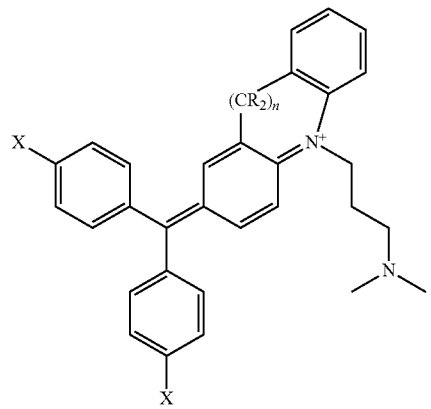

4. The composition of claim 1, wherein the compound is imipramine blue defined by formula

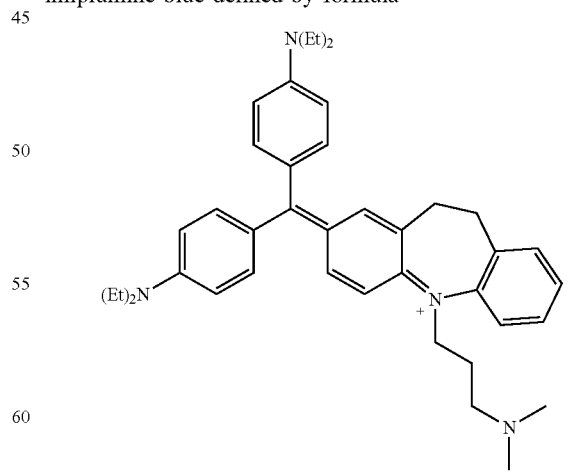

or a pharmaceutically acceptable salt thereof.

* * * * *